(12) United States Patent
Jacobson et al.

(10) Patent No.: US 10,975,406 B2
(45) Date of Patent: Apr. 13, 2021

(54) DIRECTED ENDONUCLEASES FOR REPEATABLE NUCLEIC ACID CLEAVAGE

(71) Applicant: Massachusetts Institute of Technology, Cambridge, MA (US)

(72) Inventors: Joseph M. Jacobson, Newton, MA (US); Noah Michael Jakimo, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/800,096

(22) Filed: Jul. 15, 2015

(65) Prior Publication Data

US 2016/0017393 A1    Jan. 21, 2016

Related U.S. Application Data

(60) Provisional application No. 62/026,577, filed on Jul. 18, 2014.

(51) Int. Cl.
| | |
|---|---|
| C12N 9/22 | (2006.01) |
| C07K 19/00 | (2006.01) |
| C12P 19/34 | (2006.01) |

(52) U.S. Cl.
CPC .............. *C12P 19/34* (2013.01); *C12N 9/22* (2013.01); *C07K 2319/00* (2013.01); *C07K 2319/81* (2013.01); *C12N 2310/20* (2017.05)

(58) Field of Classification Search
None
See application file for complete search history.

(56) References Cited

PUBLICATIONS

Guilinger et al., Fusion of catalytically inactive Cas9 to FokI nuclease improves the specificity of genome modification, Nat. Biotechnol., Apr. 25, 2014, 32, 577-83.*
Bitinaite et al., FokI dimerization is required for DNA cleavage, Proc. Natl. Acad. Sci. USA, 1998, 95, 10570-75.*
Mino et al., Efficient double-stranded DNA cleavage by artificial zinc-finger nucleases composed of one zinc-finger protein and a single-chain FokI dimer, J. Biotechnol., 2009, 140, 156-61.*
Porteus et al., Gene targeting using zinc finger nuclease, Nature Biotechnol., 2005, 23, 967-73.*
Ran et al., Double Nicking by RNA-Guided CRISPR Cas9 for Enhanced Genome Editing Specificity, Cell, 2013,154, 1380-89.*
Kim et al., Hybrid restriction enzymes: Zinc finger fusions to Fok I cleavage domain, Proc. Natl. Acad. Sci. USA, 1996, 93, 1156-60.*
Ramalingam et al., Creating Designed Zinc-Finger Nucleases with Minimal Cytotoxicity, J. Mol. Biol., 2001, 405, 630-41.*
Santiago et al., Targeted gene knockout in mammalian cells by using engineered zinc-finger nucleases, Proc. Natl. Acad. Sci. USA, 2008, 105, 5809-14.*
Shalem et al., Genome-scale CRISPR-Cas9 knockout screening in human cells, Science ,Dec. 12, 2013, science.1247005.*
Sun et al., A single-chain TALEN architecture for genome engineering, Mol. BioSyst., 2014, 10, 446-53.*
Wu et al., Genome-wide binding of the CRISPR endonuclease Cas9 in mammalian cells, Nature Biotechnol., Apr. 20, 2014, 32, 670-76.*
Uniprot, Accession No. Q99ZW2, 2014, www.uniprot.org.*
Sander et al., CRISPR-Cas systems for editing, regulating and targeting genomes, Nature Biotech. 4, 2014, 348-55. (Year: 2014).*
Guo et al., Directed Evolution of an Enhanced and Highly Efficient FokI Cleavage Domain for Zinc Finger Nucleases, J. Mol. Biol. 400, 2010, 96-107. (Year: 2010).*
Tsai, S.Q., et al., "Dimeric CRISPR RNA-Guided FokI Nucleases for Highly Specific Genome Editing," Nature Biotechnology, 32(6), pp. 569-577(Jun. 2014).
Guilinger, J.P., et al., "Fusion of Catalytically Inactive Cas9 to FokI Nuclease Improves the Specificity of Genome Modification," Nature Biotechnology, 32(6): pp. 577-624 (Jun. 2014).
Sun and Zhao, "A Single-Chain TALEN Architecture for Genome Engineering," Molecular BioSystems, Electronic Supplement Material for Molecular Biosystems, Royal Society of Chemistry 10, pp. 1-11 (2003).
Minczuk, M., et al., "Development of a Single-Chain, Quasi-Dimeric Zinc-Finger Nuclease for the Selective Degradation of Mutated Human Mitochondrial DNA," Nucleic Acids Research, 36(12); pp. 3926-3938 (2008).
Ramirez, C., et al., "Engineered Zinc Finger Nickases Induce Homology-Directed Repair with Reduced Mutagenic Effects," Nucleic Acids Research, 40(12); pp. 5560-5568 (2012).
Betermier, M., et al., "Is Non-Homologous End-Joining Really and Inherently Error-Prone Process?," PLOS Genetics 10(1), pp. 1-9 (2014).
Metzger, M., et al., "Single-Strand Nicks Induce Homologous Recombination with Less Toxicity than Double-Strand Breaks Using an AAV Vector Template," Nucleic Acids Research 39(3); pp. 926-935 (2011).
Miller, J.C., et al., "An Improved Zinc-Finger Nuclease Architecture for Highly Specific Genome Editing," Nature Biotechnology 25(7), pp. 778-785 (2007).
Polo, S.E., Jackson, S.P., "Dynamics of DNA Damage Response Proteins at DNA Breaks: A Focus on Protein Modifications," Genes and Development 25, pp. 409-433 (2011).

(Continued)

*Primary Examiner* — Robert B Mondesi
*Assistant Examiner* — Todd M Epstein
(74) *Attorney, Agent, or Firm* — Elmore Patent Law Group, P.C.; Carolyn Elmore; Joseph Zucchero

(57) ABSTRACT

The invention provides compositions and methods for repeatable directed endonucleases (RDEs) and methods for repeatedly, and specifically cleaving DNA offset from the RDE's DNA recognition sequence on the target nucleic acid rather than within the DNA recognition sequence. Conservation of the recognition sequence of the target nucleic acid enables for re-localization of an RDE back to the DNA recognition sequence for further cleavage. The RDEs and methods of the invention are useful in applications including, but not limited to, recording data into a genome, timing the order of biochemical pathway events, efficient genome engineering and encoding lagged cellular death.

18 Claims, 15 Drawing Sheets

Specification includes a Sequence Listing.

(56) References Cited

PUBLICATIONS

Beurdeley, M., et al., "Compact Designer TALENs for Efficient Genome Engineering," Nature Communications, pp. 1-8 (2013).
Gabsalilow, L., et al., "Site- and Strand-Specific Nicking of DNA by Fusion Proteins Derived from MutH and I-Scel or TALE Repeats," Nucleic Acids Research 41(7): pp. 1-11 (2013).
Lee, M.N., et al., "Common Genetic Variants Modulate Pathogen-Sensing Responses in Human Dendritic Cells," Science 343, pp. 1119-1131 (2014).
Redding, S., Greene, E.C, "How do Proteins Locate Specific Targets in DNA?," Chemical Physics Letters 570, pp. 1-11 (2013).
Nemudryi, A., et al., "TALEN and CRISPR/Cas Genome Editing Systems: Tools of Discovery," Acta Naturae 6(3): pp. 19-40 (2014).

\* cited by examiner dCas9 (D10A and H840A):
MDKKYSIGLAIGTNSVGWAVITDEYKVPSKKFKVLGNTDRHSIKKNLIGALLFDSGETAE
ATRLKRTARRRYTRRKNRICYLQEIFSNEMAKVDDSFFHRLEESFLVEEDKKHERHPIF
GNIVDEVAYHEKYPTIYHLRKKLVDSTDKADLRLIYLALAHMIKFRGHFLIEGDLNPDNS
DVDKLFIQLVQTYNQLFEENPINASGVDAKAILSARLSKSRRLENLIAQLPGEKKNGLFG
NLIALSLGLTPNFKSNFDLAEDAKLQLSKDTYDDDLDNLLAQIGDQYADLFLAAKNLSDA
ILLSDILRVNTEITKAPLSASMIKRYDEHHQDLTLLKALVRQQLPEKYKEIFFDQSKNGYA
GYIDGGASQEEFYKFIKPILEKMDGTEELLVKLNREDLLRKQRTFDNGSIPHQIHLGELH
AILRRQEDFYPFLKDNREKIEKILTFRIPYYVGPLARGNSRFAWMTRKSEETITPWNFEE
VVDKGASAQSFIERMTNFDKNLPNEKVLPKHSLLYEYFTVYNELTKVKYVTEGMRKPA
FLSGEQKKAIVDLLFKTNRKVTVKQLKEDYFKKIECFDSVEISGVEDRFNASLGTYHDLL
KIIKDKDFLDNEENEDILEDIVLTLTLFEDREMIEERLKTYAHLFDDKVMKQLKRRRYTG
WGRLSRKLINGIRDKQSGKTILDFLKSDGFANRNFMQLIHDDSLTFKEDIQKAQVSGQG
DSLHEHIANLAGSPAIKKGILQTVKVVDELVKVMGRHKPENIVIEMARENQTTQKGQKN
SRERMKRIEEGIKELGSQILKEHPVENTQLQNEKLYLYYLQNGRDMYVDQELDINRLSD
YDVDAIVPQSFLKDDSIDNKVLTRSDKNRGKSDNVPSEEVVKKMKNYWRQLLNAKLIT
QRKFDNLTKAERGGLSELDKAGFIKRQLVETRQITKHVAQILDSRMNTKYDENDKLIRE
VKVITLKSKLVSDFRKDFQFYKVREINNYHHAHDAYLNAVVGTALIKKYPKLESEFVYGD
YKVYDVRKMIAKSEQEIGKATAKYFFYSNIMNFFKTEITLANGEIRKRPLIETNGETGEIV
WDKGRDFATVRKVLSMPQVNIVKKTEVQTGGFSKESILPKRNSDKLIARKKDWDPKKY
GGFDSPTVAYSVLVVAKVEKGKSKKLKSVKELLGITIMERSSFEKNPIDFLEAKGYKEVK
KDLIIKLPKYSLFELENGRKRMLASAGELQKGNELALPSKYVNFLYLASHYEKLKGSPE
DNEQKQLFVEQHKHYLDEIIEQISEFSKRVILADANLDKVLSAYNKHRDKPIREQAENIIH
LFTLTNLGAPAAFKYFDTTIDRKRYTSTKEVLDATLIHQSITGLYETRIDLSQLGGD (SEQ
ID NO: 1)

FIG. 12

FokI:
GSQLVKSELEEKKSELRHKLKYVPHEYIELIEIARNSTQDRILEMKVMEFFMKVYGYRG
KHLGGSRKPDGAIYTVGSPIDYGVIVDTKAYSGGYNLPIGQADEMQRYVEENQTRNKH
INPNEWWKVYPSSVTEFKFLFVSGHFKGNYKAQLTRLNHITNCNGAVLSVEELLIGGE
MIKAGTLTLEEVRRKFNNGEINF (SEQ ID NO: 2)

FIG. 13

Element Peptide or Nucleic Acid Sequences

NLS:
PKKKRKV (SEQ ID NO: 33)

dCas9(D10A and H840A):
MDKKYSIGLAIGTNSVGWAVITDEYKVPSKKFKVLGNTDRHSIKKNLIGALLFDSGETAEATRLKRTARRRYT
RRKNRICYLQEIFSNEMAKVDDSFFHRLEESFLVEEDKKHERHPIFGNIVDEVAYHEKYPTIYHLRKKLVDSTD
KADLRLIYLALAHMIKFRGHFLIEGDLNPDNSDVDKLFIQLVQTYNQLFEENPINASGVDAKAILSARLSKSRR
LENLIAQLPGEKKNGLFGNLIALSLGLTPNFKSNFDLAEDAKLQLSKDTYDDDLDNLLAQIGDQYADLFLAAK
NLSDAILLSDILRVNTEITKAPLSASMIKRYDEHHQDLTLLKALVRQQLPEKYKEIFFDQSKNGYAGYIDGGAS
QEEFYKFIKPILEKMDGTEELLVKLNREDLLRKQRTFDNGSIPHQIHLGELHAILRRQEDFYPFLKDNREKIEKI
LTFRIPYYVGPLARGNSRFAWMTRKSEETITPWNFEEVVDKGASAQSFIERMTNFDKNLPNEKVLPKHSLLY
EYFTVYNELTKVKYVTEGMRKPAFLSGEQKKAIVDLLFKTNRKVTVKQLKEDYFKKIECFDSVEISGVEDRFN
ASLGTYHDLLKIIKDKDFLDNEENEDILEDIVLTLTLFEDREMIEERLKTYAHLFDDKVMKQLKRRRYTGWGRL
SRKLINGIRDKQSGKTILDFLKSDGFANRNFMQLIHDDSLTFKEDIQKAQVSGQGDSLHEHIANLAGSPAIKKG
ILQTVKVVDELVKVMGRHKPENIVIEMARENQTTQKGQKNSRERMKRIEEGIKELGSQILKEHPVENTQLQN
EKLYLYYLQNGRDMYVDQELDINRLSDYDVDHIVPQSFLKDDSIDNKVLTRSDKNRGKSDNVPSEEVVKKMK
NYWRQLLNAKLITQRKFDNLTKAERGGLSELDKAGFIKRQLVETRQITKHVAQILDSRMNTKYDENDKLIREV
KVITLKSKLVSDFRKDFQFYKVREINNYHHAHDAYLNAVVGTALIKKYPKLESEFVYGDYKVYDVRKMIAKSE
QEIGKATAKYFFYSNIMNFFKTEITLANGEIRKRPLIETNGETGEIVWDKGRDFATVRKVLSMPQVNIVKKTEV
QTGGFSKESILPKRNSDKLIARKKDWDPKKYGGFDSPTVAYSVLVVAKVEKGKSKKLKSVKELLGITIMERSS
FEKNPIDFLEAKGYKEVKKDLIIKLPKYSLFELENGRKRMLASAGELQKGNELALPSKYVNFLYLASHYEKLK
GSPEDNEQKQLFVEQHKHYLDEIIEQISEFSKRVILADANLDKVLSAYNKHRDKPIREDAENIIHLFTLTNLGAP
AAFKYFDTTIDRKRYTSTKEVLDATLIHQSITGLYETRIDLSQLGGD (SEQ ID NO: 1)

FokI:
GSQLVKSELEEKKSELRHKLKYVPHEYIELIEARNSTQDRILEMKVMEFFMKVYGYRGKHLGGSRKPDGAIY
TVGSPIDYGVIVDTKAYSGGYNLPIGQADEMQRYVEEMQTRNKHINPNEWWKVVPSSVTEFKFLFVSGHFK
GNYKAQLTRLNHITNCNGAVLSVEELLIGGEMIKAGTLTLEEVRRKFNNGEINF (SEQ ID NO: 2)

Linker1:
SGSETPGTSESATPES (SEQ ID NO: 12)

Linker2:
SGSGSGSGSGSGSGSGGSSGGGSSGSGSGSGSGGSGSGGS (SEQ ID NO: 20)

Recognition sequence(Protospacer Adjacent Motif Protospacer Sequence):
CCNN₁N₂N₃...N₂₀ single-strand guide RNA(Spacer Scaffold based on tracrRNA):
N'₂₀N'₁₉N'₁₈...N'₃N'₂N'₁GTTTTAGAGCTAGAAATAGCAAGTTAAAATAAGGCTAGTCCGTTATCAACTTGAAAAAG
TGGCACCGAGTCGGTGCTTTTT SEQ ID NO: 38

An apostrophe denotes complementary base. Since N can represent any base, if N₁ = A, then N'₁ = T.

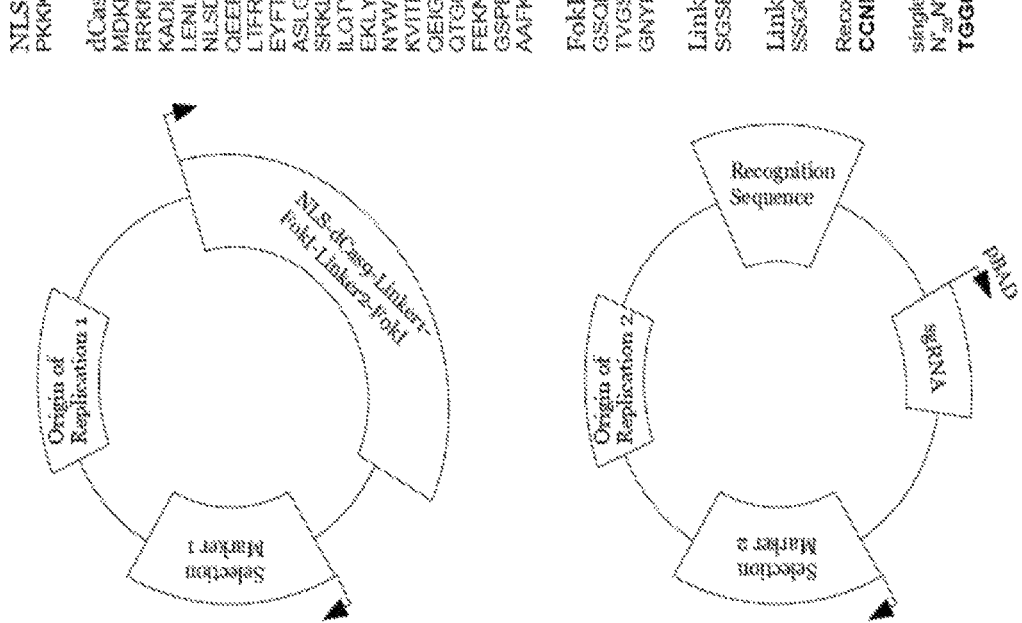

Plasmid Maps

SEQUENCE LISTING

```
<160> NUMBER OF SEQ ID NOS: 38

<210> SEQ ID NO 1
<211> LENGTH: 1368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45
```

```
Gly Ala Leu Leu Phe Asp Ser Gly Glu Thr Ala Glu Ala Thr Arg Leu
            50                  55                  60

Lys Arg Thr Ala Arg Arg Tyr Thr Arg Lys Asn Arg Ile Cys
 65              70                  75                  80

Tyr Leu Gln Glu Ile Phe Ser Asn Glu Met Ala Lys Val Asp Asp Ser
                    85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
            130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                    165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                    245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                    325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                    405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460
```

```
Met Thr Arg Lys Ser Glu Glu Thr Ile Thr Pro Trp Asn Phe Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
                610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
                690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp Ala Ile Val Pro Gln Ser Phe Leu Lys
                835                 840                 845

Asp Asp Ser Ile Asp Asn Lys Val Leu Thr Arg Ser Asp Lys Asn Arg
                850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
```

-continued

```
                885                 890                 895
Phe Asp Asn Leu Thr Lys Ala Glu Arg Gly Gly Leu Ser Glu Leu Asp
                    900                 905                 910

Lys Ala Gly Phe Ile Lys Arg Gln Leu Val Glu Thr Arg Gln Ile Thr
                    915                 920                 925

Lys His Val Ala Gln Ile Leu Asp Ser Arg Met Asn Thr Lys Tyr Asp
                    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                    965                 970                 975

Glu Ile Asn Asn Tyr His His Ala His Asp Ala Tyr Leu Asn Ala Val
                    980                 985                 990

Val Gly Thr Ala Leu Ile Lys Lys Tyr Pro Lys Leu Glu Ser Glu Phe
                    995                1000                1005

Val Tyr Gly Asp Tyr Lys Val Tyr Asp Val Arg Lys Met Ile Ala
                    1010                1015                1020

Lys Ser Glu Gln Glu Ile Gly Lys Ala Thr Ala Lys Tyr Phe Phe
                    1025                1030                1035

Tyr Ser Asn Ile Met Asn Phe Phe Lys Thr Glu Ile Thr Leu Ala
                    1040                1045                1050

Asn Gly Glu Ile Arg Lys Arg Pro Leu Ile Glu Thr Asn Gly Glu
                    1055                1060                1065

Thr Gly Glu Ile Val Trp Asp Lys Gly Arg Asp Phe Ala Thr Val
                    1070                1075                1080

Arg Lys Val Leu Ser Met Pro Gln Val Asn Ile Val Lys Lys Thr
                    1085                1090                1095

Glu Val Gln Thr Gly Gly Phe Ser Lys Glu Ser Ile Leu Pro Lys
                    1100                1105                1110

Arg Asn Ser Asp Lys Leu Ile Ala Arg Lys Lys Asp Trp Asp Pro
                    1115                1120                1125

Lys Lys Tyr Gly Gly Phe Asp Ser Pro Thr Val Ala Tyr Ser Val
                    1130                1135                1140

Leu Val Val Ala Lys Val Glu Lys Gly Lys Ser Lys Lys Leu Lys
                    1145                1150                1155

Ser Val Lys Glu Leu Leu Gly Ile Thr Ile Met Glu Arg Ser Ser
                    1160                1165                1170

Phe Glu Lys Asn Pro Ile Asp Phe Leu Glu Ala Lys Gly Tyr Lys
                    1175                1180                1185

Glu Val Lys Lys Asp Leu Ile Ile Lys Leu Pro Lys Tyr Ser Leu
                    1190                1195                1200

Phe Glu Leu Glu Asn Gly Arg Lys Arg Met Leu Ala Ser Ala Gly
                    1205                1210                1215

Glu Leu Gln Lys Gly Asn Glu Leu Ala Leu Pro Ser Lys Tyr Val
                    1220                1225                1230

Asn Phe Leu Tyr Leu Ala Ser His Tyr Glu Lys Leu Lys Gly Ser
                    1235                1240                1245

Pro Glu Asp Asn Glu Gln Lys Gln Leu Phe Val Glu Gln His Lys
                    1250                1255                1260

His Tyr Leu Asp Glu Ile Ile Glu Gln Ile Ser Glu Phe Ser Lys
                    1265                1270                1275

Arg Val Ile Leu Ala Asp Ala Asn Leu Asp Lys Val Leu Ser Ala
                    1280                1285                1290
```

```
Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 2
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gly Ser Gln Leu Val Lys Ser Glu Leu Glu Glu Lys Lys Ser Glu Leu
1               5                   10                  15

Arg His Lys Leu Lys Tyr Val Pro His Glu Tyr Ile Glu Leu Ile Glu
                20                  25                  30

Ile Ala Arg Asn Ser Thr Gln Asp Arg Ile Leu Glu Met Lys Val Met
            35                  40                  45

Glu Phe Phe Met Lys Val Tyr Gly Tyr Arg Gly Lys His Leu Gly Gly
50                  55                  60

Ser Arg Lys Pro Asp Gly Ala Ile Tyr Thr Val Gly Ser Pro Ile Asp
65                  70                  75                  80

Tyr Gly Val Ile Val Asp Thr Lys Ala Tyr Ser Gly Tyr Asn Leu
                85                  90                  95

Pro Ile Gly Gln Ala Asp Glu Met Gln Arg Tyr Val Glu Glu Asn Gln
                100                 105                 110

Thr Arg Asn Lys His Ile Asn Pro Asn Glu Trp Trp Lys Val Tyr Pro
            115                 120                 125

Ser Ser Val Thr Glu Phe Lys Phe Leu Phe Val Ser Gly His Phe Lys
130                 135                 140

Gly Asn Tyr Lys Ala Gln Leu Thr Arg Leu Asn His Ile Thr Asn Cys
145                 150                 155                 160

Asn Gly Ala Val Leu Ser Val Glu Glu Leu Leu Ile Gly Gly Glu Met
                165                 170                 175

Ile Lys Ala Gly Thr Leu Thr Leu Glu Glu Val Arg Arg Lys Phe Asn
            180                 185                 190

Asn Gly Glu Ile Asn Phe
            195

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Ser Gly Gly Ser Gly Gly Ser
1               5
```

```
<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Ser Gly Gly Ser Gly Gly Ser Gly Gly Ser Gly Gly Ser Gly
1               5                   10                  15

Gly Ser

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met Lys Ile Ile Glu Gln Leu Pro Ser Ala
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Arg His Lys Leu Arg Lys Arg Val Gly Ser
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Pro Phe Leu Leu Glu Pro Asp Asn Ile Asn Gly Lys Thr Cys
1               5                   10                  15

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly His Gly Thr Gly Ser Thr Gly Ser Gly Ser Ser
1               5                   10

<210> SEQ ID NO 9
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 9

Met Ser Arg Pro Asp Pro Ala
1               5

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Ser Ala Gly Ser Ala Ala Gly Ser Gly Glu Phe
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Gly Ser Glu Thr Pro Gly Thr Ser Glu Ser Ala
1               5                   10

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Gly Ser Glu Thr Pro Gly Thr Ser Glu Ser Ala Thr Pro Glu Ser
1               5                   10                  15

<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Gly Ser Glu Thr Pro Gly Thr Ser Glu Ser Ala Thr Pro Glu Gly
1               5                   10                  15

Gly Ser Gly Gly Ser
            20

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Gly Ser Met
```

```
<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Gly Gly Gly Ser Gly Gly Gly Ser Gly Gly Gly Ser Ser
1               5                   10

<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Ser Gly Gly Gly Gly Ser Gly Gly Gly Gly Ser Gly Gly Gly Gly
1               5                   10                  15

Ser Gly

<210> SEQ ID NO 17
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Ser Gly Gly Gly Gly Ser Gly Gly Gly Gly Ser Gly Gly Gly Gly
1               5                   10                  15

Ser Gly Gly Gly Gly Ser
            20

<210> SEQ ID NO 18
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Ser Gly Gly Gly Gly Ser Gly Gly Gly Gly Ser Gly Gly Gly Gly
1               5                   10                  15

Ser Gly Gly Gly Gly Ser Gly Gly Gly Gly Ser
            20                  25

<210> SEQ ID NO 19
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Ser Gly Gly Gly Ser Gly Gly Gly Ser Gly Gly Gly Ser Gly Gly
1               5                   10                  15
```

```
Gly Ser Gly Gly Gly Ser Gly Gly Gly Ser
        20              25
```

<210> SEQ ID NO 20
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Ser Ser Gly Gly Gly Ser Gly Gly Gly Ser Gly Gly Gly Ser Gly Gly
1               5                   10                  15
Gly Ser Ser Gly Gly Gly Gly Ser Gly Gly Gly Ser Gly Gly Gly Ser
            20                  25                  30
```

<210> SEQ ID NO 21
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Gly Ser Gly Ser Arg Ser Ala Pro Glu Ala Met Tyr Ala Pro Asp Ala
1               5                   10                  15
Val Lys Met Val His Glu Phe Gly Gly Ser Asn Tyr Thr Gly Met Thr
            20                  25                  30
Ile Lys Met Ser Thr Ser Leu Thr Val Thr Asp Glu Gly Ser Ser His
        35                  40                  45
Thr Thr Gln Pro His Ala Glu Asn Thr Arg Arg Asp Asp Gln Asn Ile
    50                  55                  60
Gly Ser Arg Phe Ala Gly Glu Ser His Val Asn Asn Thr Thr Lys Thr
65                  70                  75                  80
Thr Thr Leu Glu Glu Gly Ser Gly Ser Gly Gly
                85                  90
```

<210> SEQ ID NO 22
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Gly Ser Gly Ser Gly Ser Thr Pro Trp Lys Pro Ile Ile Ala Arg His
1               5                   10                  15
Asp Arg Arg Arg Pro Leu Ser Thr Gly Ser Gly Ser Gly Ser Gly
            20                  25                  30
```

<210> SEQ ID NO 23
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Gly Ser Gly Ser Gly Ser Ile Thr Arg Thr Thr Asn Pro Arg Asn Val
```

```
            1               5                   10                  15
Val Pro Lys Ile Tyr Met Ser Ala Gly Ser Ile Pro Leu Thr Thr His
            20                  25                  30

Ile Thr Asn Ser Ile Gln Pro Thr Leu Trp Thr Ile Gly Ser Ile Asn
            35                  40                  45

Gly Val Ala Pro Leu Ala Lys Ser Ile Lys Leu Gly Ile Pro Val Thr
  50                  55                  60

Gly Ser Ala Tyr Thr Asp Gln Thr Thr Ala Met Val Arg Lys Val
 65                  70                  75                  80

Ser Val Phe Met Gly Ser Gly Ser Gly Ser Gly
                    85                  90

<210> SEQ ID NO 24
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gly Ser Gly Ser Gly Ser Met Asn Lys Met Gln Pro Asn Trp Thr Phe
1               5                   10                  15

Thr Trp Gln Ala Asn Ser Leu Ile Gly Ser Gly Ser Gly Ser Gly
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gly Ser Arg Phe Ala Gly Glu Ser His Val Asn Thr Thr Lys Thr
1               5                   10                  15

Thr Lys Leu Glu Gly Ser Gly Ser Ser Gly Ser Gly Ser Ser
            20                  25                  30

<210> SEQ ID NO 26
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gly Ser Gly Ser Gly Ser Thr His Arg Lys Arg His Pro Pro Met Thr
1               5                   10                  15

Lys Glu Val Ile Pro Pro Thr Ala Gly Ser Lys Val Val Lys Pro Asn
            20                  25                  30

Leu Pro Thr Asn Asn Ala Arg Ile Arg Trp Asn Ile Gly Ser Thr Leu
            35                  40                  45

Thr Val Trp Thr Ser Val Thr Asn Met Gln Gln Glu Phe Thr Thr Thr
  50                  55                  60

Gly Ser Gly Ser Gly Ser Gly
 65                  70

<210> SEQ ID NO 27
```

```
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gly Ser Gly Ser Gly Ser Asn Tyr Ala Ala Lys Pro Ile Pro Ser Ala
1               5                   10                  15

Gly Gln Leu Glu Thr Ser His Asn Gly Ser Gly Ser Gly Ser Gly
            20                  25                  30

<210> SEQ ID NO 28
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gly Ser Gly Ser Gly Ser Thr Thr Arg Arg Trp Pro Pro Gly Arg Pro
1               5                   10                  15

Asn Gln Leu Arg Asn Leu Thr Thr Gly Ser Gly Ser Gly Ser Gly
            20                  25                  30

<210> SEQ ID NO 29
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Ser Gly Ser Gly Ser Ala Thr Met Thr Ala Asn Phe Gln Val Asn
1               5                   10                  15

Ser Lys Pro Ile Thr Ser Pro Asp Gly Ser Gly Ser Gly
            20                  25

<210> SEQ ID NO 30
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gly Ser Gly Ser Gly Ser Ala Pro Glu Ala Met Tyr Ala Pro Asp Ala
1               5                   10                  15

Val Lys Met Val His Glu Phe Gly Gly Ser Asn Tyr Thr Gly Met Thr
            20                  25                  30

Ile Lys Met Ser Thr Ser Leu Thr Val Thr Asp Glu Glu Ser Ser His
        35                  40                  45

Thr Thr Gln Pro Arg Ala Glu Asn Thr Arg Arg Asp Asp Gln Asn Ile
    50                  55                  60

Gly Ser Arg Phe Ala Gly Glu Ser His Val Asn Asn Thr Thr Lys Thr
65                  70                  75                  80

Thr Lys Leu Glu Gly Ser Gly Ser Gly Lys Arg Leu Glu Pro Leu Pro
                85                  90                  95

Asp Pro Ser Asp
```

```
                 100

<210> SEQ ID NO 31
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Ser Gly Ser Gly Ser Thr Ile Leu Lys Arg Tyr Ser Leu Lys Asn
1               5                   10                  15

Glu Gln Pro Arg Ala Leu His Ile Gly Ser Gly Ser Gly
            20                  25

<210> SEQ ID NO 32
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gly Ser Gly Ser Gly Ser Val Leu Met Thr Leu Ile Asp Arg Ala Thr
1               5                   10                  15

Ala Ser Thr Lys Pro Lys Asp Ala Gly Ser Ala His Lys Gly Met Pro
            20                  25                  30

His Ala Arg Pro Arg Pro Trp Ala Ser Ser Thr Val Gly Ser Gly Thr
        35                  40                  45

Leu Thr Lys Ile Phe
    50

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Pro Lys Lys Lys Arg Lys Val
1               5

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(12)
<223> OTHER INFORMATION: Any amino acid

<400> SEQUENCE: 34

Lys Arg Xaa Xaa Xaa Xaa Xaa Xaa Xaa Xaa Xaa Xaa Lys Lys Lys Leu
1               5                   10                  15

<210> SEQ ID NO 35
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 35

Pro Lys Lys Asn Arg Leu Arg Arg Pro
1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Pro Leu Leu Lys Lys Ile Lys Gln
1               5

<210> SEQ ID NO 37
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Ser Gly Gly Gly Gly Ser Gly Gly Gly Ser Gly Gly Gly Gly Ser
        35                  40                  45

<210> SEQ ID NO 38
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, t, g, unknown or other

<400> SEQUENCE: 38
nnnnnnnnnn nnnnnnnnnn gttttagagc tagaaatagc aagttaaaat aaggctagtc      60
cgttatcaac ttgaaaaagt ggcaccgagt cggtgctttt t                         101
```

DIRECTED ENDONUCLEASES FOR REPEATABLE NUCLEIC ACID CLEAVAGE

RELATED APPLICATION

This application claims the benefit of U.S. Provisional Application No. 62/026,577, filed on Jul. 18, 2014. The entire teachings of the above application are incorporated herein by reference.

BACKGROUND OF THE INVENTION

Directed endonucleases localize on a specific DNA recognition sequence where they cleave one of both strands of DNA to create a single-strand break (SSB) or double-strand break (DSB). Examples of directed endonucleases include Zinc Finger Nucleases (ZFNs), Transcription Activator Like Effector Nucleases (TALENs), and proteins, like Cas9, associated with Clustered Regularly Interspaced Palindromic Repeats (CRISPR). Zinc Fingers and Transcription Activator Like Effectors are proteins with peptide sequences designed for binding to its corresponding DNA recognition sequence. The native repair pathways of such breaks in cells as well as identification and engineering of more efficient directed endonucleases have allowed recent art to advance the field of genome engineering and synthetic biology.

Recently the prior art has provided new artificial combinations of directed endonucleases fused to less specific nuclease domains (Tsai et al. (2014) *Nature Biotechnology*; doi:10.1038/nbt.2908; Guilinger et al., *Nature Biotechnology* (2014) doi:10.1038/nbt.2909; Sun and Zhao (2014) *Mol. BioSyst.*, 10:446; Minczuk et al., *Nucleic Acids Research*, 2008, 36:3926-3938; Ramirez et al., *Nucleic Acids Research*, 2012, doi.1093/nar/gks179.

It would be desirable to use existing and new directed endonuclease variants and directed endonuclease fusion proteins for use in designing and using self-repeating and highly specific, sequence dependent changes to a targeted region of DNA.

SUMMARY OF THE INVENTION

The invention provides compositions and methods for repeatable directed endonucleases (RDEs) and methods for repeatedly, and specifically cleaving DNA offset from the RDE's DNA recognition sequence on the target nucleic acid rather than within the DNA recognition sequence. Conservation of the recognition sequence of the target nucleic acid enables for re-localization of an RDE back to the DNA recognition sequence for further cleavage. The RDEs and methods of the invention are useful in applications including, but not limited to, recording data into a genome, timing the order of biochemical pathway events, efficient genome engineering and encoding lagged cellular death.

BRIEF DESCRIPTION OF THE DRAWINGS

FIG. 12 is the amino acid sequence of dCas9 (SEQ ID NO: 1).

FIG. 13 is the amino acid sequence of FokI (SEQ ID NO: 2).

FIG. 14 is a plasmid map of one preferred RDE of the invention.

DETAILED DESCRIPTION OF THE INVENTION

Figure 1:
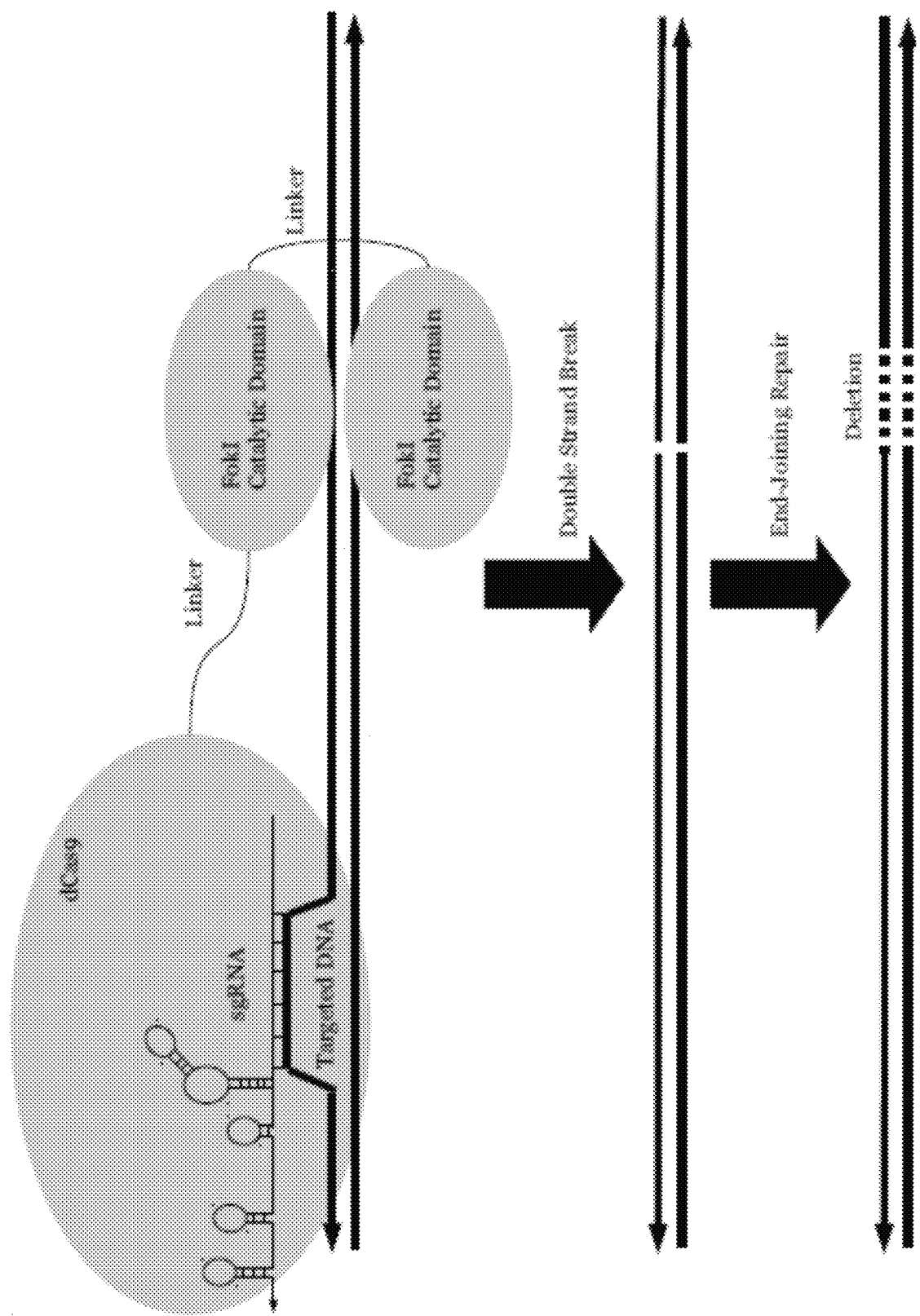
FIG. 1 is a diagram of single chain dCas9-FokI-FokI for repeatable cleavage offset to recognition sequence.

The invention provides compositions and methods using RDEs for repeatedly cleaving DNA at a roughly fixed number of base pairs offset from a RDE's DNA recognition sequence. Cutting events can thereby initiate DNA repair end joining pathways that result in a short deletion of base pairs from the position of cleavage. The break in DNA is repaired by native end joining processes, such as Non-Homologous End Joining (NHEJ) or Alternative End Joining (AEJ), which often remove a base from the DNA break. Thus, additional localization events cause additional removal of bases adjacent to the recognition sequence.

In one embodiment, the present invention provides repeatable directed endonucleases (RDEs) comprising all or a functional fragment of a directed endonuclease fused to all or a functional fragment of a nuclease domain via an amino acid linker sequence. Any directed endonuclease or directed endonuclease binding domain known to those skilled in the art may be used as a DNA-recognition domain (DRD) in the practice of the present invention. Examples of DRDs include, but are not limited to, Zinc Finger Nucleases (ZFNs), Transcription Activator Like Effector Nucleases (TALENs), and proteins, like Cas9 when associated with a specific guide RNA (Cas9-gRNA), of the Clustered Regularly Interspaced Palindromic Repeats (CRISPR) system. Cas9 of the CRISPER system contains wild type DNA-cleaving activity when complexed with a specific guide RNA (referred to herein as "gRNA" or "sgRNA") molecule for targeted DNA-binding. An engineered variant of Cas9 called deactivated (dCas9) has a loss of DNA-cleaving function. dCas9 in combination with its gRNA is a particularly preferred DRD of the present invention.

As used herein, a "functional fragment" of a DRD, nuclease domain or any other protein, polypeptide or nucleic acid as referenced in this application, is a protein, polypeptide or nucleic acid whose sequence is not identical to the full-length protein, polypeptide or nucleic acid, yet retains the same or has enhanced function as compared to the full-length protein, polypeptide or nucleic acid. Additionally, a functional fragment may have lesser function than the full-length protein, polypeptide or nucleic acid, but still have adequate function as defined by the user. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. The ability of a protein to interact with another protein can be determined, for example, by co-immunoprecipitation, two-hybrid assays or complementation, both genetic and biochemical. Functional fragments of DRDs may comprise at least about 50% sequence similarity with a native binding domain sequence, at least about 60-70%, and at least about 80%-90% or greater sequence similarity with, a native binding domain to retain sufficient binding activity. Such a variant binding domain may include one or more of: an N- or C-terminal truncation, one or more amino acid substitutions, deletions or insertions, or modification of an amino acid, for example, modification of an amino acid side chain entity.

Figure 10:
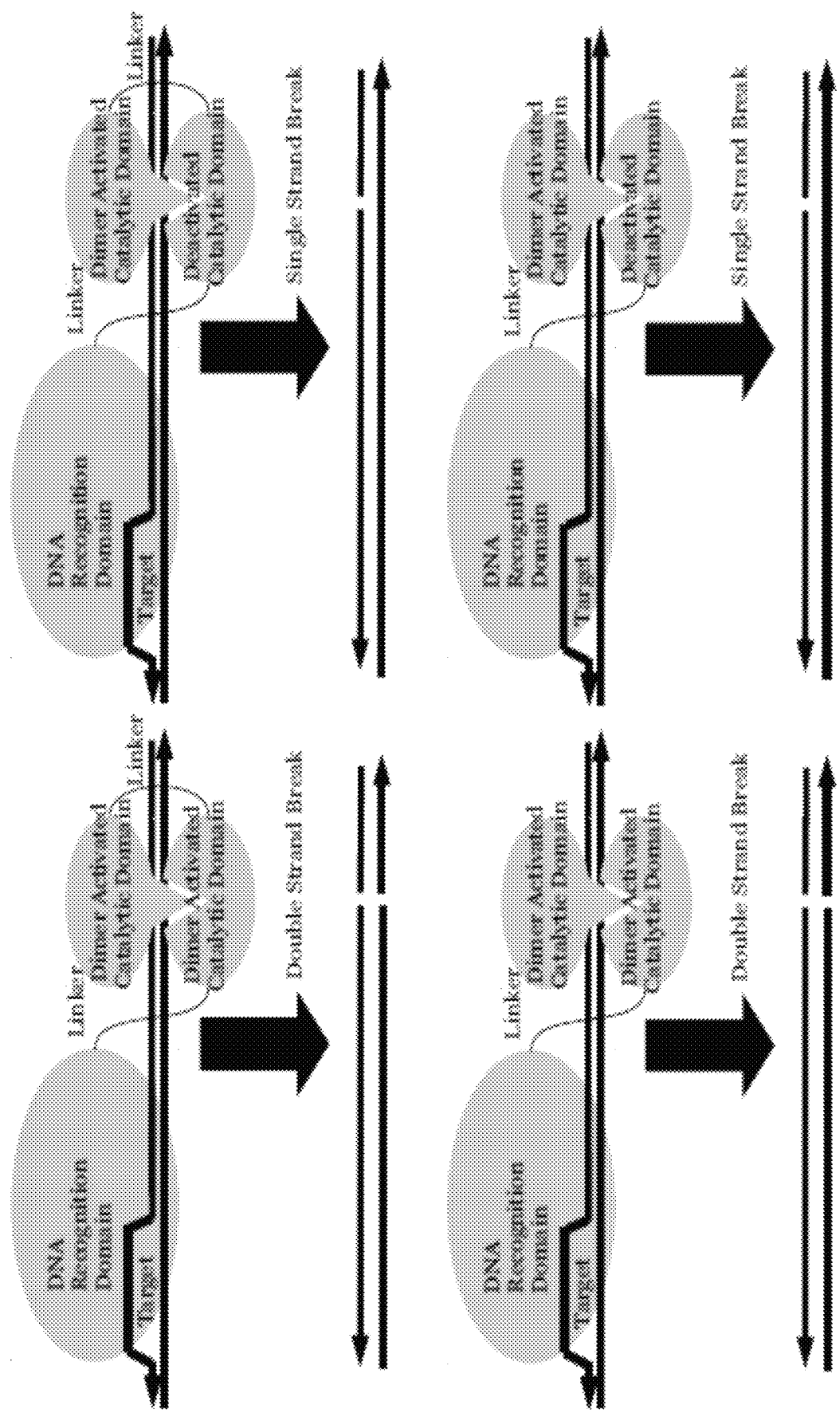
FIG. 10 is a diagram of alternative embodiments of the invention using any DRD with HEs and REs that activate upon heterodimerization to create either SSBs or DSBs in DNA.

In a preferred embodiment, the DRD is selected from the group consisting of Zinc Finger Nucleases (ZFNs), Transcription Activator Like Effector Nucleases (TALENs), or dCas9 associated with a guide RNA. In a preferred embodiment the DRD is dCAS9 associated with a guide RNA. FIG. 10 shows an amino acid sequence dCas9 (SEQ ID NO: 1; Guilinger et al., *Nature Biotechnology* (2014) doi:10.1038/nbt.2909).

As used herein, "nuclease domain" (also referred to herein as a catalytic domain or an induction domain) is a domain responsible for physical cleavage of DNA strands and may introduce either single stranded or double-stranded breaks. The introduction of a single stranded break in DNA is also referred to as a "nick" or "nicking" of the DNA. Examples of nuclease domains include homing endonucleases (HEs) or restriction enzymes (REs). HEs include, but are not limited to, NucA, TevI, I-SceI and ColE7. REs include, but are not limited to, for example FokI, PvuII, NdeI, BsrBI, BsaI, and MMeI. Engineered derivatives and functional fragments of any of these REs and HEs can work as monomers, heterodimers, or homodimers for cleaving on one or both strands of DNA. In a preferred embodiment the nuclease domain is FokI. An exemplary amino acid sequence for FokI is SEQ ID NO: 2; Guilinger et al., *Nature Biotechnology* (2014) doi:10.1038/nbt.2909).

Examples of variant nuclease domains include N- or C-terminal truncated nuclease domains, for example, N-terminal truncations of up to about 20 amino acid residues and C-terminal truncations of up to about 15 amino acid residues, and one or more amino acid substitutions, insertions or deletions which do not adversely affect nuclease activity. Suitable amino acid substitutions include conservative amino acid substitutions, for example, substitution of an amino acid with a hydrophobic side chain with a like amino acid, e.g. alanine, valine, leucine, isoleucine, phenylalanine and tyrosine; substitution of an amino acid with an uncharged polar side chain with a like amino acid, e.g. serine, threonine, asparagine and glutamine; substitution of an amino acid having a positively charged side chain with a like amino acid, e.g. arginine, histidine and lysine; or substitution of an amino acid having a negatively charged side chain with a like amino acid, e.g. aspartic and glutamic acid. Variant nuclease domains may also include one or more modified amino acids, for example, amino acids including modified side chain entities which do not adversely affect nuclease activity.

At least a first nuclease domain is linked to a DRD via a first linking domain. The first linking domain will generally be a polypeptide of a length sufficient to permit the first nuclease domain to retain nuclease function when linked to the DRD, and also sufficient to permit the DNA-binding domain to bind the endonuclease to a target substrate but at a sufficient distance from the cleavage site of the nuclease such that the DNA recognition sequence of the DRD is preserved after cleavage of the target DNA by the nuclease. The first linking domain is not limited to, but may be from 1 amino acid residue to about 125 amino acid residues, from about 1 amino acid residue to about 95 amino acid residues, from about 1 amino acid residue to about 60 amino acid residues, from about 1 amino acid residue to about 70, from about 1 to about 60 amino acid residues, from about 1 to about 50 amino acid residues, from about 1 to about 40 amino acid residues, from about 1 to about 30 amino acid residues, or from about 1 amino acid residue to about 25 amino acid residues. The first linking domain may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 44, 45, 46, 47, 48, 49, or 50 amino acid residues in length. The length of the linker domain may be adjusted depending on the distance between the binding and cleavage sites on a target nucleic acid molecule. By including an appropriately sized linker, RDEs of the invention can cleave nucleic acid molecules where the binding and cleavage sites are separated by varying numbers of base pairs.

The linking domain may be a random sequence, for example, may be one or more glycine residues. The linking domain may be a simple repeat of amino acids, for example, GGS, which may be repeated multiple times. As used herein, such a repeat will be indicated by placing the amino acids in parenthesis and using a subscript to indicate the number of times repeated. Thus $(GGS)_6$ indicates a linking domain of six repeats of the amino acids glycine-glycine-serine. In some embodiments, the linker domain may comprise one or more glycine residues in addition to one or more other amino acid residues. The linking domain may be flexible or may comprise one or more regions of secondary structure that impart rigidity, for example, alpha helix forming sequences.

Table 1 provides example of suitable first linking domains (Guilinger et al., *Nature Biotechnology* (2014) doi:10.1038/nbt.2909).

TABLE 1

| Linker Amino Acid Sequence | SEQ ID NO: |
|---|---|
| GGSGGSGGS | 3 |
| GGSGGSGGSGGSGGSGGS | 4 |
| MKIIEQLPSA | 5 |
| VRHKLRKRVGS | 6 |
| VPFLLEPDNINGKTC | 7 |
| GHGTGSTGSGSS | 8 |
| MSRPDPA | 9 |
| GSAGSAAGSGEF | 10 |
| SGSETPGTSESA | 11 |
| SGSETPGTSESATPES | 12 |
| SGSETPGTSESATPEGGSGGS | 13 |
| GGSM | 14 |
| SGGGSGGGSGGGSS | 15 |

In one preferred embodiment, the RDE of the invention comprises a second nuclease domain fused to the C-terminus of the first nuclease domain via a second linking domain. This creates an RDE construct that is a single-chain quasi-dimeric RDE which is particularly useful when using nuclease domains that require dimer pairs for cleavage such as FokI nucleases. The second linking domain between the pair of nuclease domains is to be long enough and flexible enough to allow the formation of a intra-molecular FokI dimer for appropriate cleavage of the target nucleic acid.

In one embodiment the second linking domain may be from 1 amino acid residue to about 150 amino acid residues, from about 25 amino acid residue to about 125 amino acid residues, from about 30 amino acid residue to about 95 amino acid residues, from about 35 amino acid residue to about 70, 80, 90 or 100 amino acid residues. In one embodiment the seconding linking domain is at least 30 amino acid residues in length, preferably at least 40 amino acid residues in length and preferably at least about 50 amino acid residues in length. Other embodiments may include linkers outside of these ranges. Examples of suitable amino acid sequences for second linking domains are found in Table 2 (Sun and Zhao, 2014, *Mol. BioSyst.*, 10:446; Minczuk et al., *Nucleic Acids Research*, 2008, 36:3926-3938).

| Amino Acid Sequence | SEQ ID NO |
|---|---|
| SSGGGGSGGGGSGGGGSG | 16 |
| SSGGGGSGGGGSGGGGSGGGGS | 17 |
| SSGGGGSGGGGSGGGGSGGGGSGGGGS | 18 |
| SSGGGSGGGSGGGSGGGSGGGSGGGS | 19 |
| SSGGGSGGGSGGGSGGGSSGGGSGGGSGGGS | 20 |
| GSGSRSAPEAMYAPDAVKMVHEFGGSNYTGMTIKMS TSLTVTDEGSSHTTQPHAENTRRDDQNIGSRFAGES HVNNTTKTTTLEEGSGSG G | 21 |
| GSGSGSTPWKPIIARHDRRRPLSTGSGSGSG | 22 |
| GSGSGSITRTTNPRNVVPKIYMSAGSIPLTTHITNS IQPTLWTIGSINGVAPLAKSIKLGIPVTGSAYTDQT TAMVRKKVSVFMGSGSGSG | 23 |
| GSGSGSMNKMQPNWTFTWQANSLIGSGSGSG | 24 |
| GSRFAGESHVNNTTKTTKLEGSGSSGSGSS | 25 |
| GSGSGSTHRKRHPPMTKEVIPPTAGSKVVKPNLPTN NARIRWNIGSTLTVWTSVTNMQQEFTTTGSGSGSG | 26 |
| GSGSGSNYAAKPIPSAGQLETSHNGSGSGSG | 27 |
| GSGSGSTTRRWPPGRPNQLRNLTTGSGSGSG | 28 |
| GSGSGSATMTANFQVNSKPITSPDGSGSG | 29 |
| GSGSGSAPEAMYAPDAVKMVHEFG GSNYTGMTIKM STSLTVTDEESSHTTQPRAENTRRD DQNIGSRFAG ESHVNNTTKTTKLEGSGSGKRLEPLPDPSD | 30 |
| GSGSGSTILKRYSLKNEQPRALHIGSGSG | 31 |
| GSGSGSVLMTLIDRATASTKPKDAGSAHKGMPHARP RPWASSTVGSGTLTKIF | 32 |
| GGGGSGGGGSGGGGSGGGGSGGGGS | 37 |
| GGGGS GGGSGGGGSGGGSGGGGS | |

In some embodiments, an RDE of the invention may comprise one or more additional domains. Examples of additional domains include, but are not limited to, linking domains and functional domains. Typically, linking domains may be disposed between two functional domains, for example, between a nuclease domain and a DNA-recognition domain and also between two nuclease domains. Other functional domains include domains comprising nuclear localization signals (NLS), transcription activating domains, dimerization domains, and other functional domains known to those skilled in the art. A suitable NLS, for example is the amino acid sequence PKKKRKV (SEQ ID NO: 33); KRX$_{10}$KKKL (SEQ ID NO: 34); PKKNRLRRP (SEQ ID NO:35); and PLLKKIKQ (SEQ ID NO:36).

Preferred RDEs of the invention include, but are not limited to, a FokI nuclease or a FokI nuclease dimer pair linked to a dCas9 targeting domain, a zinc finger DNA targeting domain, or a TALEN DNA targeting domain wherein the nuclease is linked at a position that is sufficiently offset from the DNA recognition site of the target nucleic acid such that the DNA recognition site is preserved after cleavage of the target DNA by the nuclease. This allows the RDE to repeatedly relocate to the preserved recognition site and continue to cleave the target DNA until terminated in accordance with the methods of the invention.

In one preferred embodiment, the RDE comprises a single chain fusion protein comprising dCas9 linked to first FokI protein via a first linker and a second FokI protein linked to the first FokI via a second linker wherein the first linker comprises at least 5 amino acids and the second linker comprises at least 30 amino acids and wherein the first FokI protein is capable of forming a dimer pair with the second FokI protein for cleaving a target nucleic acid.

The present invention also provides nucleic acid molecules encoding the RDEs of the invention. Such molecules may be DNA or RNA. Typically, DNA molecules will comprise one or more promoter regions operably linked to a nucleic acid sequence encoding all or a portion of an RDE of the invention. Nucleic acid molecules of the invention may be provided as part of a larger nucleic acid molecule, for example, an expression vector. Suitable expression vectors include, but are not limited to, plasmid vectors, viral vectors, and retroviral vectors. Nucleic acid molecules of the invention may be provided as part of a composition, for example, a pharmaceutical composition. FIG. 14 shows a plasmid map of a preferred RDE of the invention.

The present invention also provides cells, cell lines and transgenic organisms (e.g., plants, fungi, animals) comprising one or more nucleic acid molecules of the invention. Suitable cells include, but are not limited to, mammalian cells (e.g., mouse cells, human cells, rat cells, etc.) which may be stem cells, avian cells, plant cells, insect cells, bacterial cells, fungal cells (e.g., yeast cells), and any other type of cell known to those skilled in the art.

Recombinant technology may be used to prepare the RDEs of the invention. In this regard, a DNA construct comprising DNA encoding the selected nuclease, first linking domain, second linking domain (if present), DNA-targeting domain, and any functional domains if present may be inserted into a suitable expression vector which is subsequently introduced into an appropriate host cell (such as bacterial, yeast, algal, fungal, insect, plant and mammalian) for expression. Suitable expression vectors are those vectors which will drive expression of the inserted DNA in the selected host. Typically, expression vectors are prepared by site-directed insertion of a DNA construct therein. The DNA construct is prepared by replacing a coding region, or a portion thereof, within a gene native to the selected host, or in a gene originating from a virus infectious to the host, with the endonuclease construct. In this way, regions required to control expression of the endonuclease DNA, which are recognized by the host including a promoter and a 3' region to terminate expression, are inherent in the DNA construct. To allow selection of host cells stably transformed with the expression vector, a selection marker is generally included in the vector which takes the form of a gene conferring some survival advantage on the transformants such as antibiotic resistance. Cells stably transformed with endonuclease DNA-containing vector are grown in culture media and under growth conditions that facilitate the growth of the particular host cell used. One of skill in the art would be familiar with the media and other growth conditions.

The RDEs of the invention may be made using well-established peptide synthetic techniques, for example, FMOC and t-BOC methodologies. In addition, polynucleotides disclosed herein, for example, DNA substrates and DNA encoding the present chimeric endonucleases may also be made based on the known sequence information using well-established techniques. Peptides and oligonucleotides are also commercially available.

In a further embodiment of the invention, a method of repeatedly cleaving a target nucleic acid is provided comprising the step of contacting a target nucleic acid with a repeatable directed endonuclease (RDE), wherein the RDE binds to its recognition sequence on the target nucleic acid and cleaves the target nucleic acid at a position that is offset from the RDE's recognition sequence thereby preserving the recognition sequence and wherein after the first cleavage of the target nucleic acid, the preserved recognition sequence is bound by an RDE which makes a second cleavage of the target nucleic acid sequence at a position that is offset from the RDE's recognition sequence thereby preserving the recognition sequence on the target nucleic acid. Using this method two or more relocalization events of the targeting domain of the RDE cause additional removal of bases adjacent to the recognition sequence. Placement of a gene—by means of synthetic assembly or site-specific homologous recombination—that expresses a protein or nucleic acid component of the RDE complex within the target nucleic acid can allow this process to terminate once the deleted area extends into said gene. If essential DNA is included in the detectable region of the target nucleic acid, then this process can be used to program a delayed cell death with limited cost to fitness before the deleted region extends into essential DNA. Similarly, non-essential functional DNA can be added to the detectable region for sequential control of a biochemical pathway.

The terms "DNA recognition sequence" and "DNA recognition site" are used synonymously herein and refer to a polynucleotide of a particular sequence which can be bound and cut by a given endonuclease. A polynucleotide of a given sequence may therefore be a DNA recognition sequence or DNA recognition site for one endonuclease, but may or may not be a DNA recognition sequence or DNA recognition site for another endonuclease.

Therefore, another embodiment provides a method of repeatedly cleaving a target nucleic acid comprising the step of contacting a target nucleic acid with a repeatable directed endonuclease (RDE), wherein the RDE binds to its recognition sequence on the target nucleic acid cleaves the target nucleic acid at a position that is offset from the RDE's recognition sequence thereby preserving the recognition sequence and wherein after the first cleavage of the target nucleic acid, the preserved recognition sequence is bound by an RDE which makes a second cleavage of the target nucleic acid sequence at a position that is offset from the RDE's recognition sequence thereby preserving the recognition sequence on the target nucleic acid and wherein the target nucleic acid comprises a promoter or gene for an essential element of the RDE such that when the RDE cleaves the promoter or gene, the cleaving activity of the RDE is terminated.

In one embodiment of the method, the nuclease domain is a dimer pair of nuclease domains fused in a single chain to the DRD of the RDE.

In some embodiments, the target nucleic acid may be a gene of interest in a cell. Thus, methods of the invention may be used in genomic editing applications. Typically a method of this type will comprise introducing, into the cell, one or more one RDEs of the invention that bind to a target nucleic acid sequence in the gene (or nucleic acid molecules encoding such chimeric endonuclease under conditions resulting in expression of the chimeric endonucleases), wherein the DNA-targeting domain of the endonuclease binds to the target nucleic acid sequence and the nuclease domain cleaves the target nucleic acid at a position that is offset from the DNA recognition sequence of the target nucleic acid. In some embodiments, cleavage of the gene results in disrupting the function of the gene as repair of the double-stranded break or single stranded break introduced by the RDE of the invention may result in one or more insertions and or deletions of nucleotides at the site of the break.

Turning now to FIG. 1, in a preferred embodiment of the invention, there is constitutive expression of a fusion protein consisting of dCas9 linked to two FokI catalytic homodimeric domains as a single chain. Upon the expression of single guide RNA (sgRNA), the Cas9-sgRNA complex binds to the recognition sequence and positions the linked FokI dimer at an asymmetrically offset adjacent position (Top of Figure). At this offset position, the FokI dimer cleaves DNA to leave a DSB (Middle of Figure), which is repaired by native end joining processes. These end joining processes, like NHEJ and AEJ, often result in a short deletion at the breakage (Betermier et al., 2014, PLOS Genetics 10(1):1-9) that would not extend into the recognition sequence (Bottom of Figure).

Figure 2:
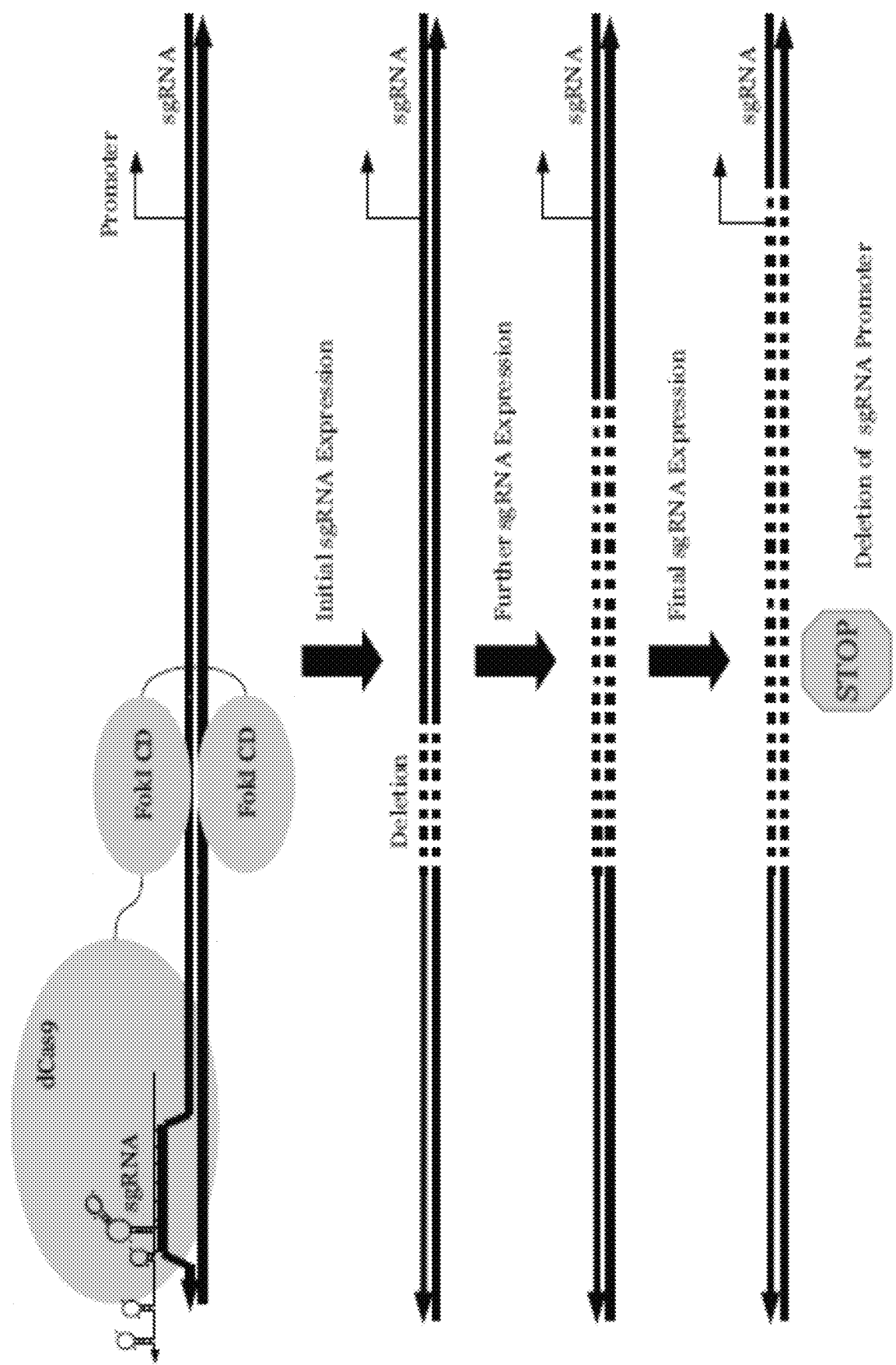
FIG. 2 is a diagram of single chain dCas9-FokI-FokI for repeatable cleavage offset to recognition sequence including a gene for a component of the DRD within the deletable region to halt extension of the deletion. The "deletable region" as used herein should be taken to mean the nucleic acid sequence in the direction of the offset that is positioned between the recognition sequence and the nearest genetic element that is essential for further targeting on the recognition sequence or replication of DNA containing the recognition sequence.

As shown in FIG. 2, the preferred embodiment of FIG. 1 continues to cut asymmetrically offset at roughly the same distance from the recognition sequence of the DRD as expression continues for the entire active DRD-RE/HE complex. Extension of the resulting deleted region is constrained by including in the deletable region the genetic element transcribing a DNA-recognition conferring component in the complex. For the preferred embodiment illustrated in FIG. 1, the simplest example would be to include a constitutively driven guide RNA under the U6 promoter. As shown, this can be a promoter and sgRNA pair for the illustrated preferred embodiment. Thus, deletions extending into this element prevent continued localization of the DRD-RE/HE complex to its target recognition sequence. Before deletions extend into the described additional element, use of pathway inducible or repressible promoters in this element can provide a correlation between the length of the deleted region and the activity of the pathway's associated signals. Measurement of the deleted region can be accomplished through fragment size analysis, NGS sequencing, fluorescent in situ hybridization or sequencing, as well as through expression patterns encoded in the deletable region. The inherent stochastic nature of DNA-binding guarantees variability in the length of the deleted region in individual cells of a population. The average length can be calculated for the population to measure the time integral of RDE expression. However, variability can also be used to generate sequence diversity among single-cells and can be applied to cell barcoding.

Figure 3:
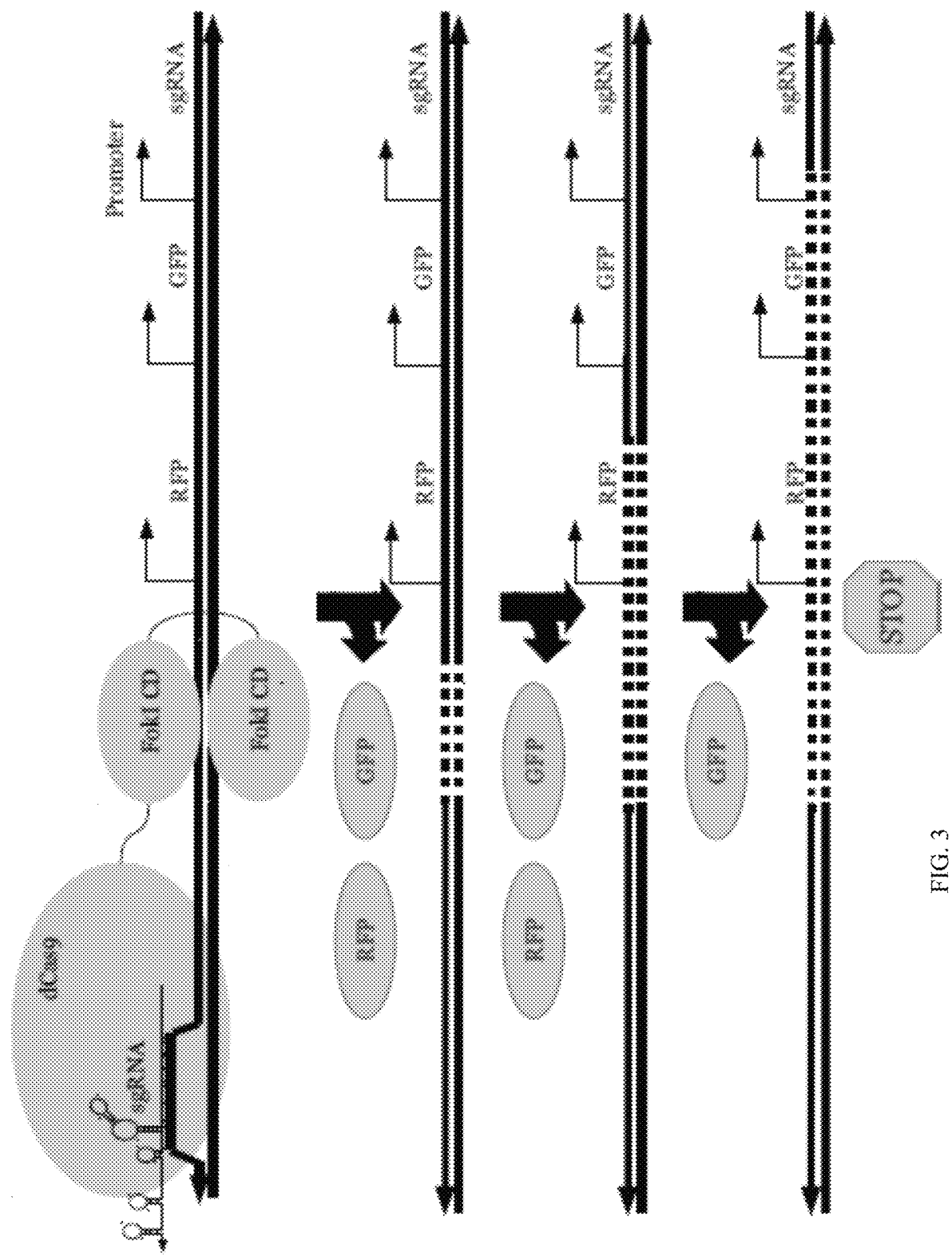
FIG. 3 is a diagram of single chain dCas9-FokI-FokI for repeatable cleavage offset to recognition sequence showing sequential control of gene expression by including ordered functional non-essential DNA in the deletable region.

As shown in FIG. 3 the deletable region can be an endogenous or synthetic sequence. Furthermore, the deletable region can include multiple functional genetic elements. Such functional elements can be used for programmable progression of gene expression. As shown, the deletable region contains RFP and GFP under separate promoters. Partial deletion of the RFP gene, which comes earlier in the deletable region than that of GFP, eliminates further RFP expression and therefore provides optical feedback for an upper bound on the length of the deleted region. Similarly, when the deleted region extends to GFP, observed loss of GFP expression lowers the upper bound of the length of the deletion.

Figure 4:
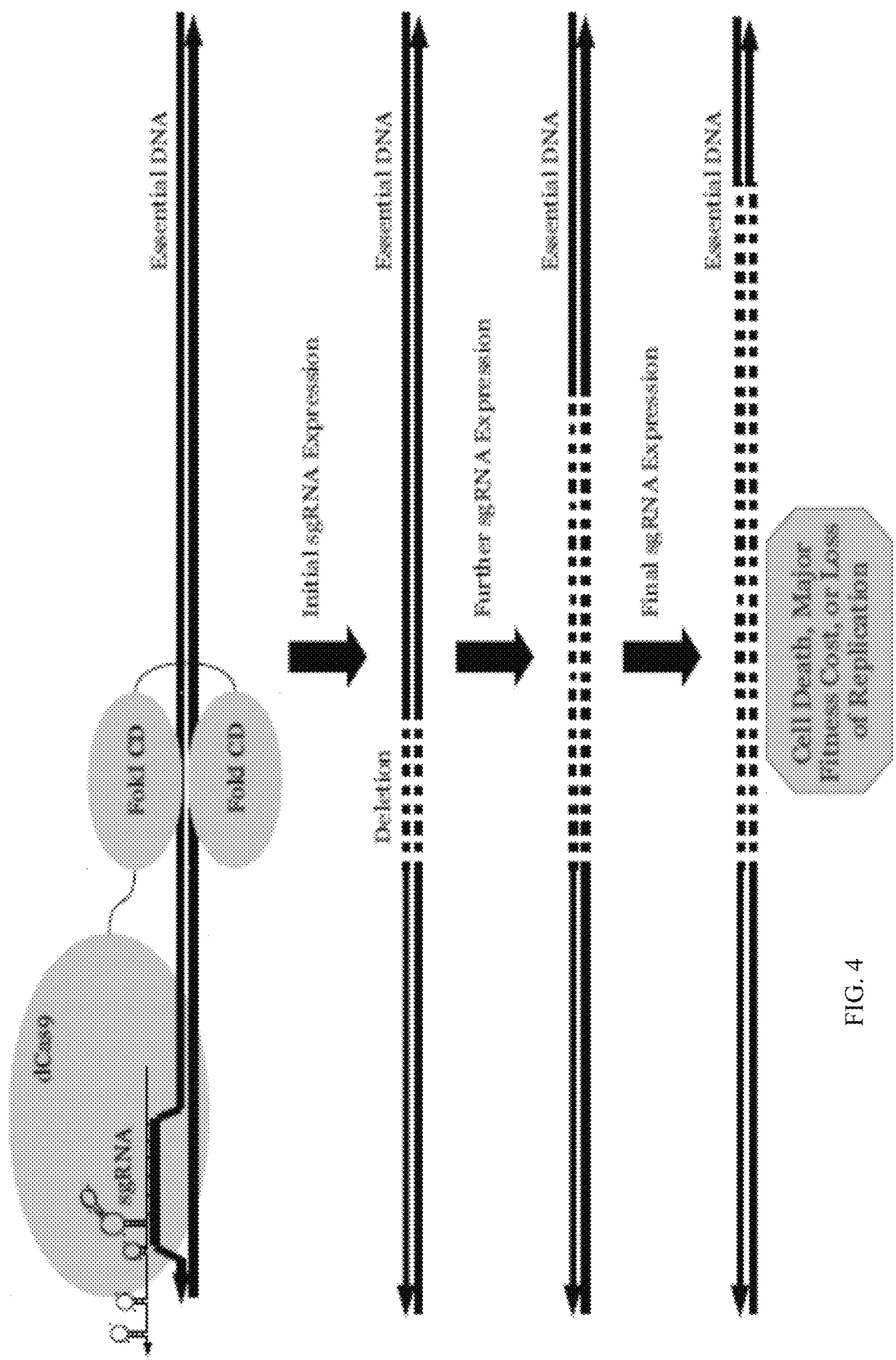
FIG. 4 is a diagram of single chain dCas9-FokI-FokI for repeatable cleavage offset to recognition sequence including essential DNA within the deletable region for delayed cell death, reduction of fitness, or replication.

As shown in FIG. 4, without including a genetic element to prevent further cleavage, the deleted region ultimately extends into DNA essential for the cell or for the replication of plasmid DNA. Such essential DNA can be endogenous, such as a polymerase gene or a plasmid's origin of replication. Essential DNA can also be inserted sequence, such as a gene for drug resistance. Cell death, a drastic reduction of fitness, or preventing a plasmid's replication are potential results of deleting such DNA. Design of the length of the region between the DNA recognition site of the target and essential DNA enables a programmable delay in the outcome of the latter's removal.

Figure 5:
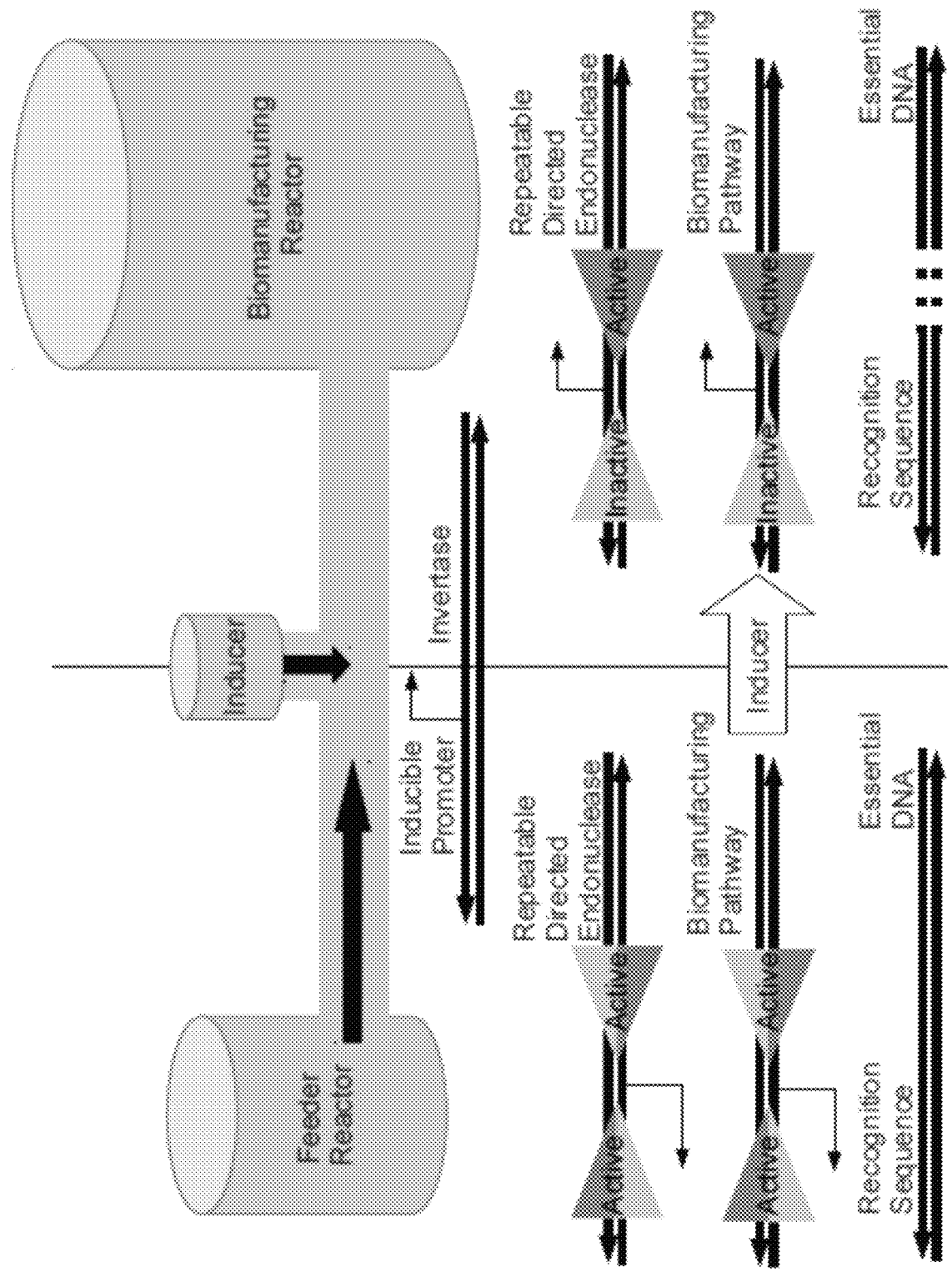
FIG. 5 is a diagram of a system for improving efficiency in biomanufacturing through limiting the number of mutations an industrial strain can propagate by programming delayed cell death.

FIG. 5 provides a schematic showing that biomanufacturing efficiency is reduced when mutations in an industrial microorganism result in an increase in fitness, but a decrease in efficiency for synthesizing a desired product. Fixation of such mutations in the population can be eliminated by constraining the number of generations that can follow from a microorganism's replication. As shown, invertase and unidirectional recombination site pairs (e.g. Cre and LoxP) can be used to invert promoters while the microorganism flows from the feeder to manufacturing reactors; Thereby initiating both repeatable offset asymmetric cleavage and the metabolic pathway for manufacturing. Many other inducers and transcriptional control pairs can be used (e.g. small molecule and light-activated transcription factors). Inside the manufacturing reactor, eventual extension of the deletable region to essential DNA in an individual microorganism results in a drastic cost to its fitness, such that the microorganism cannot propagate its mutations.

Figure 6:
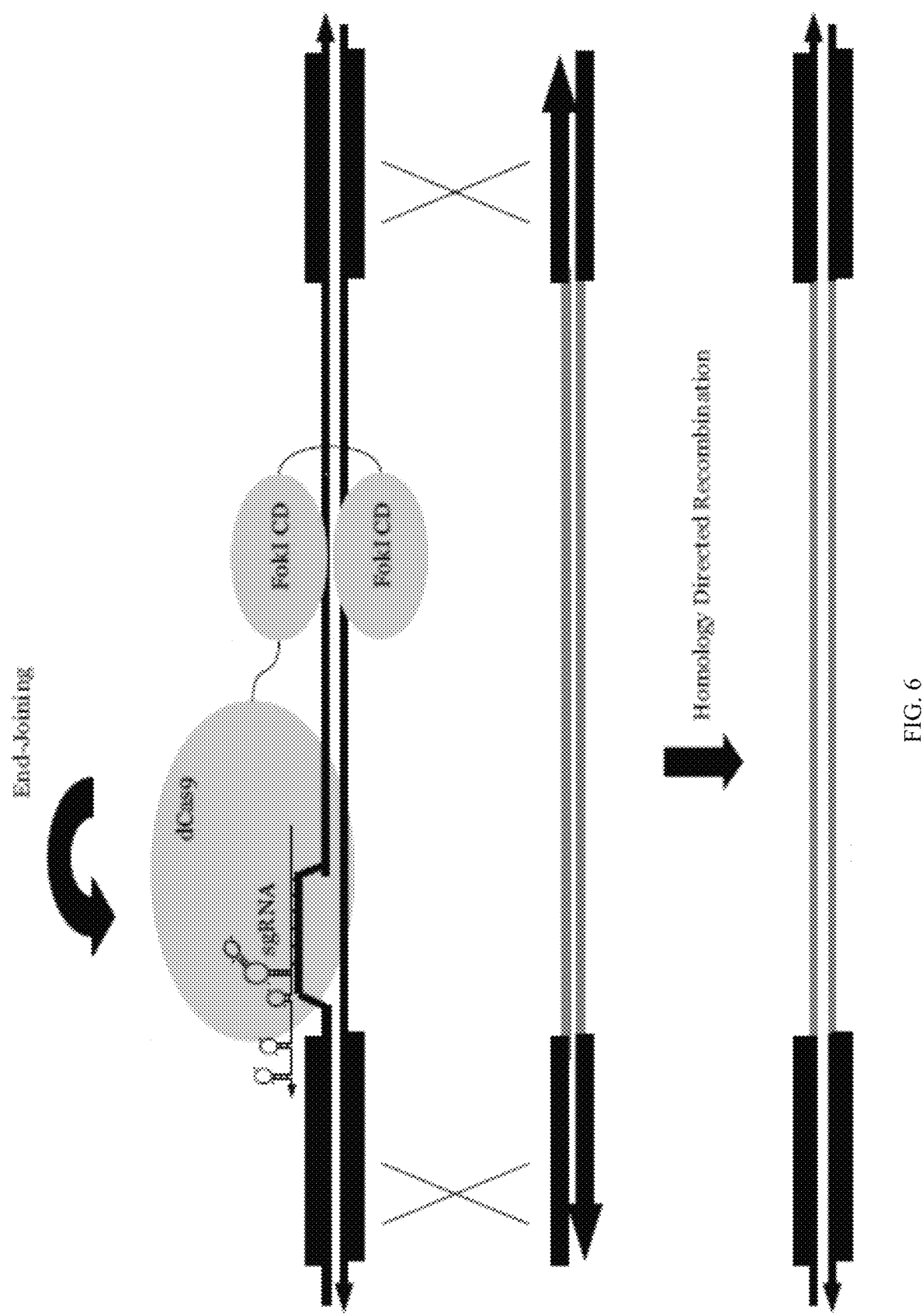
FIG. 6 is a diagram of single chain dCas9-FokI-FokI for repeatable cleavage offset to recognition sequence showing repeatable asymmetric cleavage for efficient homologous directed recombination.

FIG. 6 shows that for site-specific mutations with nucleic acid templates (middle strand of FIG. 6) in DRD-based genome engineering, the process of homology-directed repair (HDR) (also known as homologous recombination) competes with faster end joining processes that typically delete part of the recognition sequence in the repair of a DNA break. What's more, once the recognition sequence is removed, rate of HDR can be nearly negligible. As shown, repeatable cleavage asymmetrically offset from a DNA recognition sequence can preserve the recognition sequence to allow for HDR and end joining to compete again and again, until the occurrence of HDR. This technique may be most-valuable for multiplexed genome engineering for multiple loci. Alternative embodiments for genome engineering are covered in the following two figures.

Figure 7A:
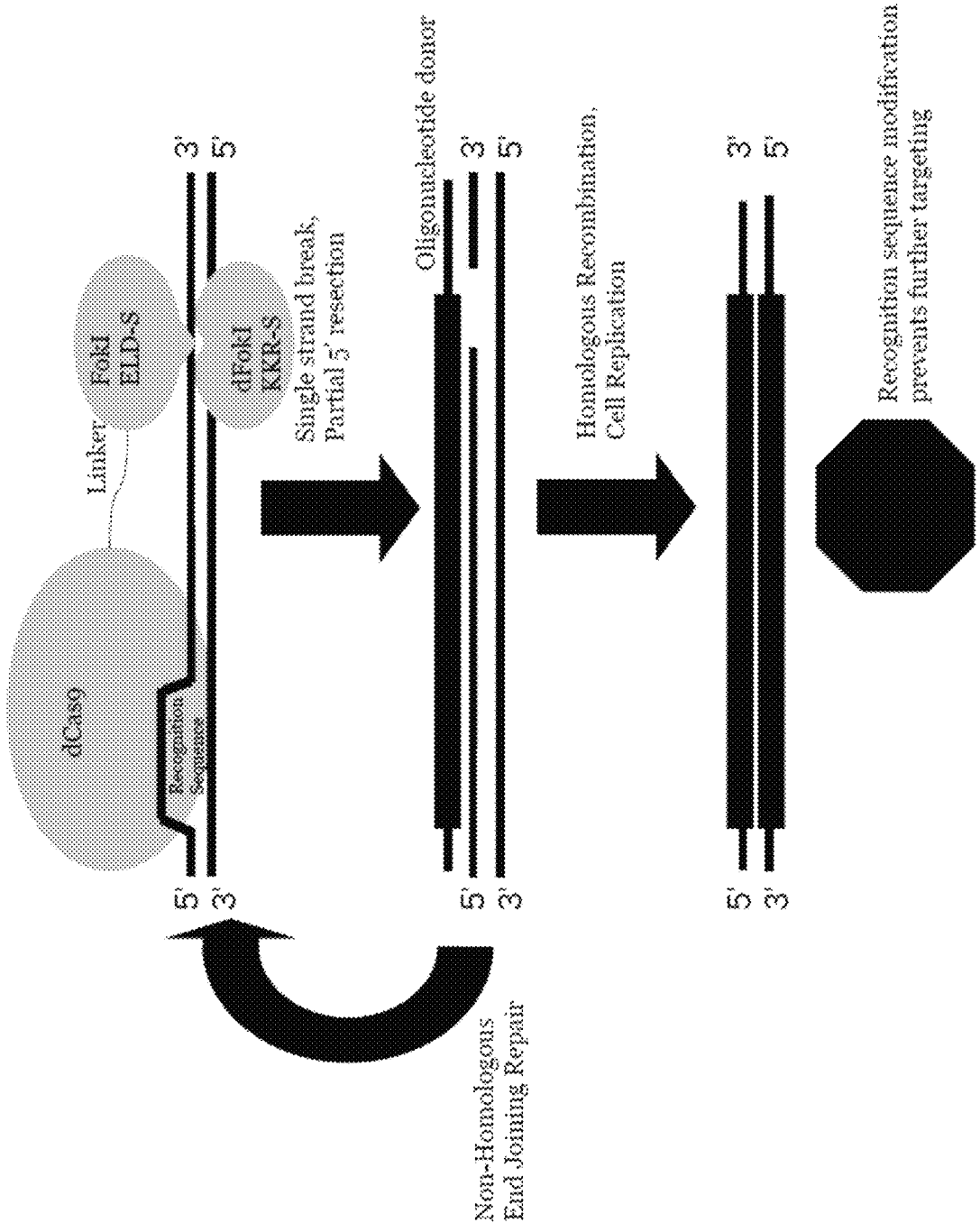
FIGS. 7A and 7B are diagrams of single chain RDEs for efficient homologous recombination induced by one or a pair of single-strand breaks.

FIG. 7A is a diagram of a system consisting of guide RNA, single-chain dCas9-FokI(ELD-S)-dFokI(KKR-S) and an oligonucleotide donor to achieve homologous recombination on a targeted position on the genome. Note, the ELD-S and KKR-S are a heterodimeric FokI pair, and dFokI denotes a variant consisting of a mutation that eliminates cleavage activity on one strand of the FokI dimer-DNA complex. Therefore, the single chain FokI(ELD-S)-dFokI (KKR-S) domain only induces a nick (or single-stranded break) in a DNA molecule. In the presence of an oligonucleotide donor, homologous recombination pathways result in a genome editing event templated by the donor strand that can also modify the recognition sequence to prevent further nicks. Such repair is described in Metzger et al., *Nucleic Acids Research*; doi: 10.1093/nar/gkq826. If the nick instead results in non-homologous end joining, then the DNA recognition site is maintained to allow for further nicking events until achieving the desired genomic edits.

Figure 7B:
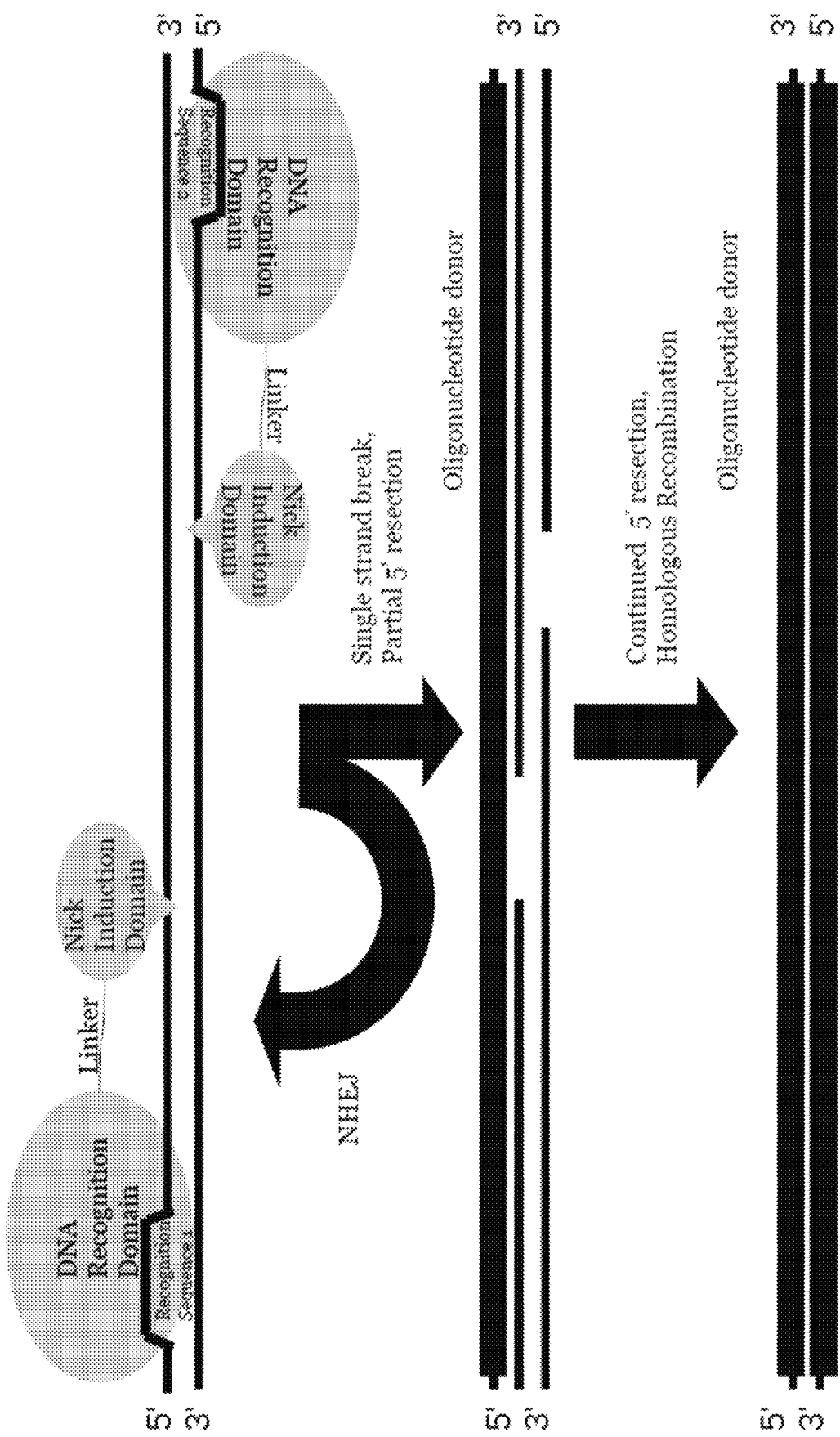
Figure 8A:
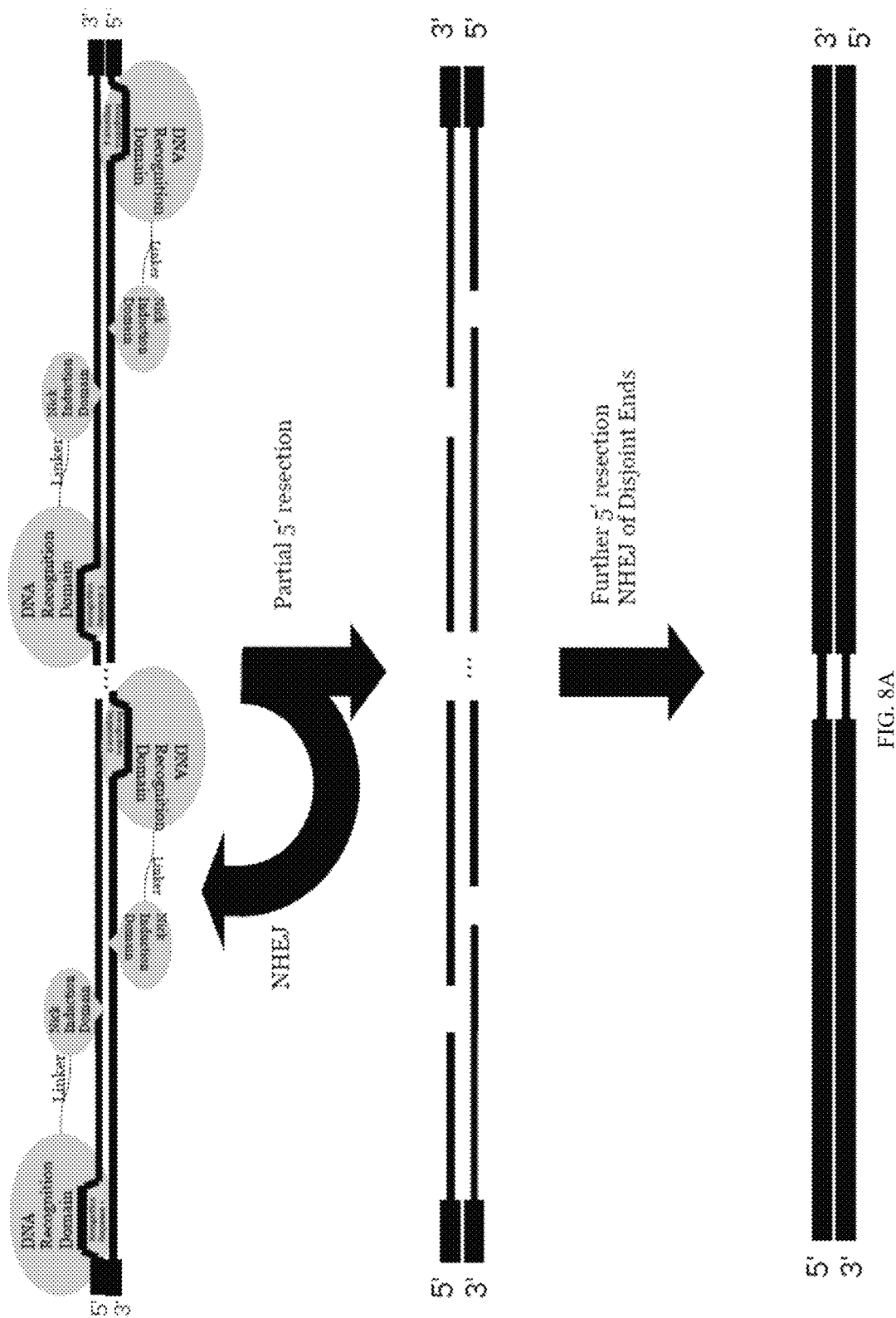
FIGS. 8A and 8B are diagrams of single chain RDEs for efficient genomic excisions induced by pairs of single-strand breaks or a pair of double-strand breaks.

FIG. 7B is a diagram of a system similar to that of FIG. 7A, but includes an additional single-chain nicking repeatable directed endonuclease (RDE). Orienting the pair such that offset nicks are interior to the DNA recognition domain enables a double-strand break to form when the resected ends of DNA meet. Again, the presence of an oligonucleotide donor allows for genome editing via homologous recombination. FIG. 8A is a diagram of a system similar to that of FIG. 7B, but includes an additional pair of single-chain nicking RDEs and lacks an oligonucleotide donor. Simultaneous formation of single-stranded (or double-stranded) breaks within each pairs can result in large genomic excisions when the exterior ends from each break are joined via non-homologous end joining.

Figure 8B:
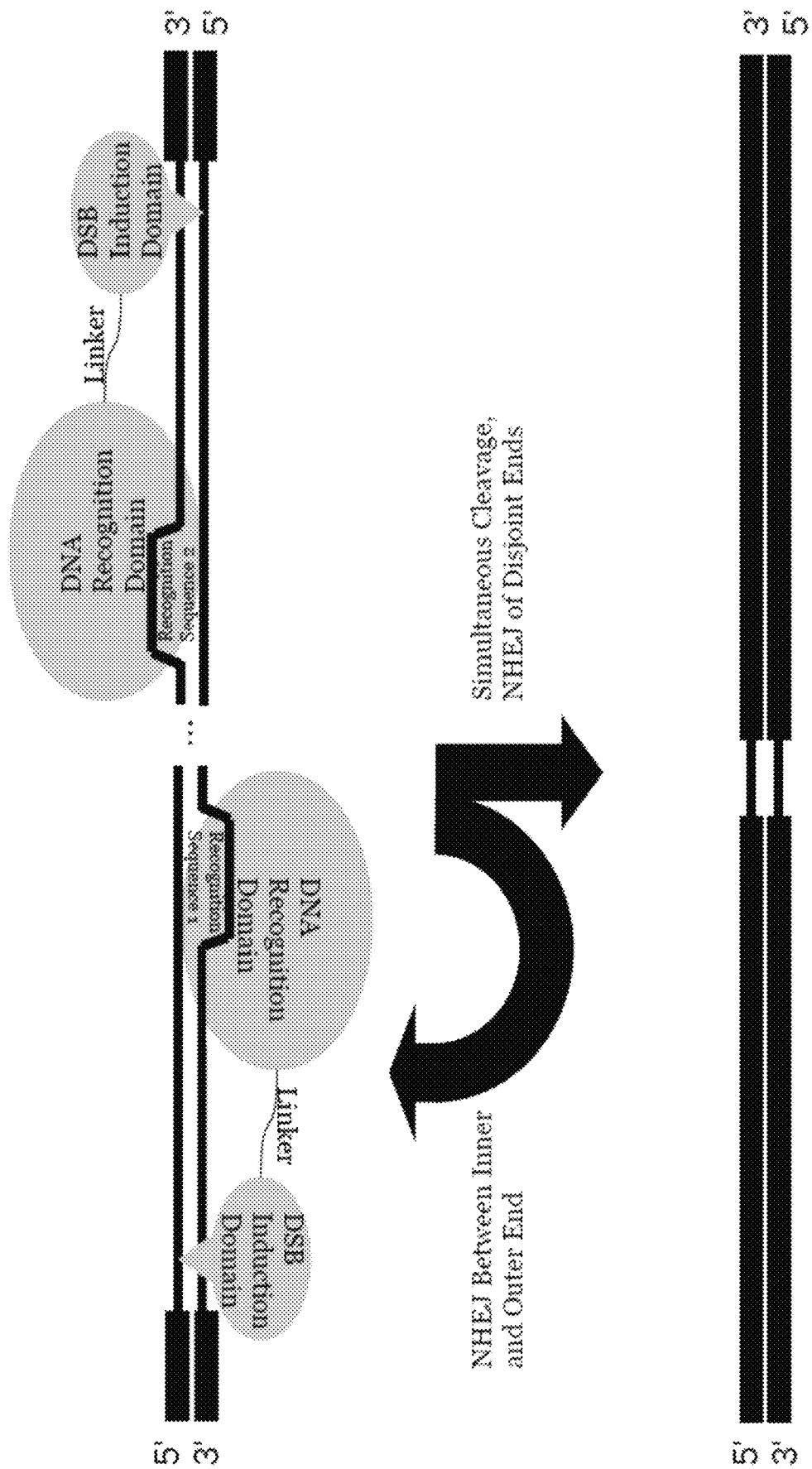

FIG. 8B is a diagram of a system consisting of two single-chain cleaving repeatable directed endonuclease (RDE). Orienting the pair such that offset double-strand breaks are exterior to the DNA recognition domain can result in large genomic excisions when the breaks occur simultaneously. Furthermore, both recognition domains are deleted by the excision.

Figure 9:
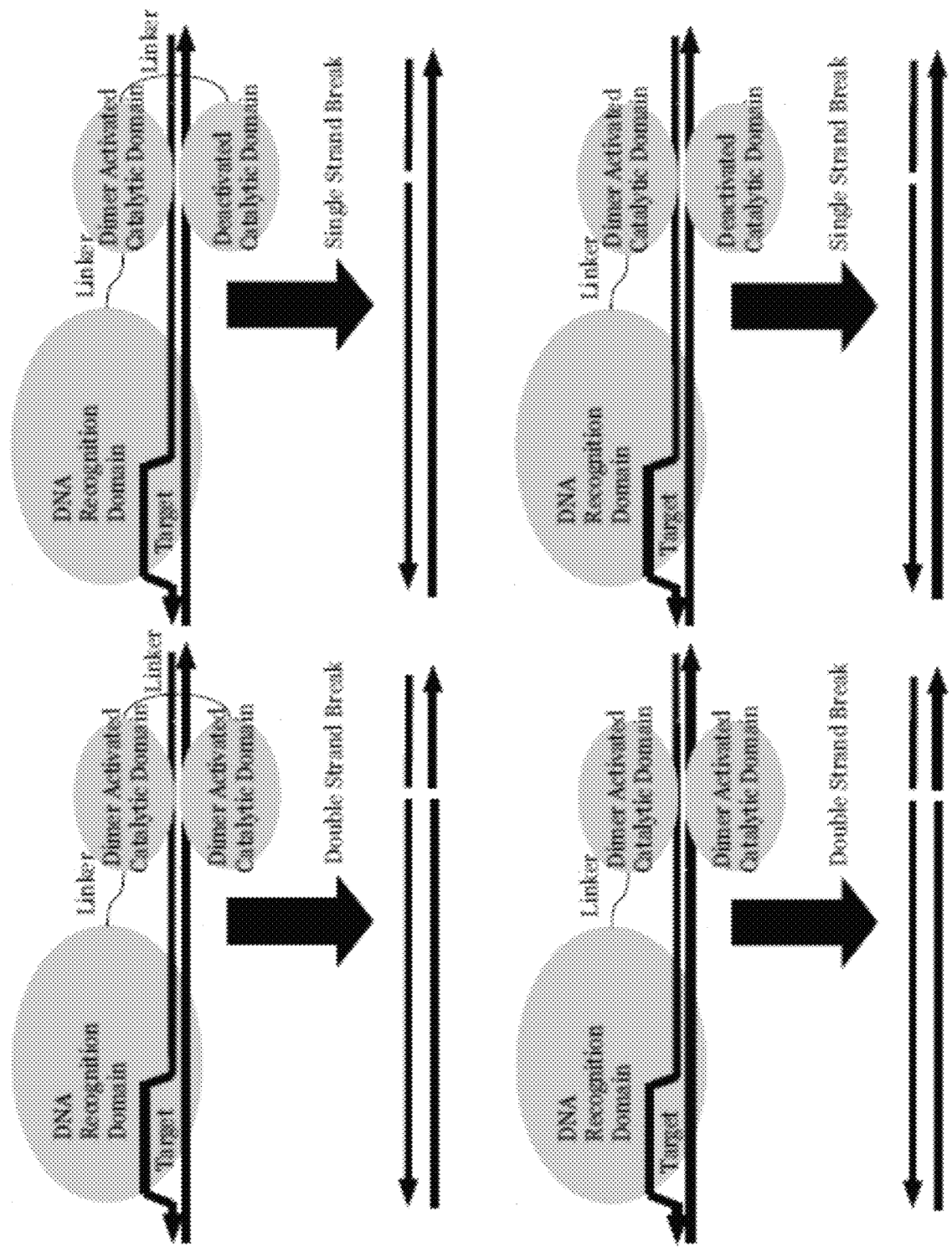
FIG. 9 is a diagram of alternative embodiments of the invention using any DRD with HEs and REs that activate upon homodimerization to create either SSBs or DSBs in DNA.

FIG. 9 provides additional preferred embodiments achieve DSBs and SSBs with homodimer-activated catalytic domains. Shown in the top left, the preferred embodiment of FIG. 9 is generalized to encompass any combination of the aforementioned DRDs and homodimer-activated catalytic RE/HE domains for creating a DSB. As shown in the Bottom Left, one preferred embodiment links only one RE/HE domain to the DRD. The two embodiments illustrated on the right achieve single-strand breaks similar to the double-strand breaking embodiments on the right, but instead have one of the homodimer catalytic domains deactivated as described in Ramirez et al., 2012, *Nucleic Acids Research*, pp. 1-9; doi:10.1093/nar/gks/179.

FIG. 10 shows additional preferred embodiments to achieve DSBs and SSBs like those of FIG. 9, but instead with heterodimer-activated catalytic domains. A FokI based example of engineering such heterodimeric domains is described in Miller et al., 2007, *Nature Biotechnology*, 25:778-785. The link between the DNA binding domain is shown linked to a catalytic domain on the opposite strand as illustrated in FIG. 9 to reflect that the target site can be on either strand and the linker can be on either termini of the DNA binding domain. Since resection occurs in the 5'-3' direction (Polo and Jackson, 2011, *Genes & Development*, 24: 409-433), deletions as a result of SSB can be made unidirectionally away from the recognition sequence.

Figure 11:
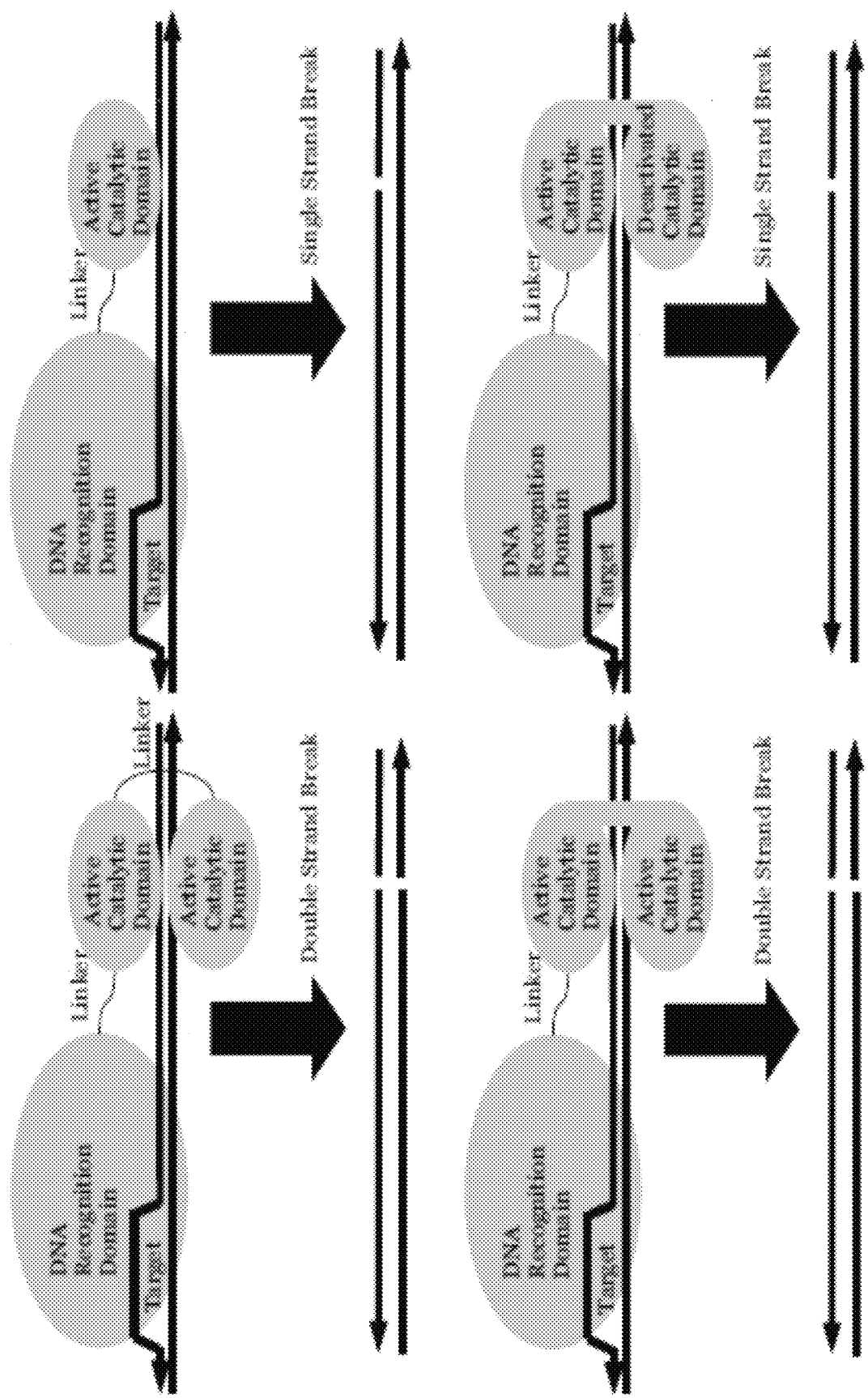
FIG. 11 is a diagram of alternative embodiments of the invention using any DRD with HEs and REs that do not require dimerization to create either single or double-strand breaks in DNA.

FIG. 11 shows additional preferred embodiments achieve DSBs and SSBs with catalytic domains that do not require dimerization for activity such as TevI (Beurdeley et al., 2013, *Nature Communications*; doi: 10/1038/ncomms2782) and I-SceI (Gabsalilow et al., *Nucleic Acids Research*, 2013, 41; doi: 10/1093/nar/gkt080) are dimeric and monomeric examples, respectively, of such catalytic domains.

FIGS. 12, 13, and 14 include peptide or nucleic acid sequences used for a preferred embodiment of the invention and two plasmid maps that can be used for such an embodiment. In the illustrated example guide RNA is expressed under the control of a pBAD promoter that is induced by the sugar arabinose. A deletion directly downstream of the recognition sequence growing towards the sgRNA is the result of multiple or continued exposures to arabinose. Said deletion no longer extends after removing the sgRNA—a component necessary for localizing the DRD-RE/HE complex to the recognition sequence.

The ability for an RDE of the invention to repeatedly cleave a nucleic acid target can be determined using well-established techniques, such as next-generation sequencing and PCR-based fragment analysis. Adaptations of recently developed techniques, such as fluorescent in situ hybridization (Lee et al, *Science*, 2014, 343; doi: 10.1126/science.1250212) and microfluidic DNA curtions (Redding and Greene, *Chemical Physical Letters*, 2013; doi: 10.1016/j.cplett.2013.03.035), are alternative readouts compatible with the invention.

The RDEs and methods of the invention are useful for example, i) for monitoring activation, exposure or synthesis of biomolecules as described in FIGS. 2 and 12; ii) for sequential control of genetic pathways as described in FIG. 3; iii) for programmable delayed cell death, loss of fitness or plasmid loss as described in FIG. 4; iv) for containment of engineered organisms as described in FIG. 4; v) for population control in biomanufacturing as described in FIG. 5; and vi) for genome engineering as described in FIG. 6, FIG. 7A-7B, and FIG. 8A-8B.

The present invention also provides kits comprising nucleic acid molecules encoding the RDE described above and a substrate for the RDE. In another embodiment, the invention provides kits comprising the RDEs of the invention. Kits of the invention can be used for genomic editing using the methods described above.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

What is claimed is:

1. A method for repeatedly cleaving a target nucleic acid in cells, cell lines, and transgenic organisms, comprising the following steps:
   i) providing cells, cell lines, and transgenic organisms comprising:
      a) one or more repeatable directed single-chain endonucleases (RDEs), wherein said RDE comprises a DNA-recognition domain that retains the ability to bind DNA but does not have, or has lost, an associated endonuclease activity that cleaves DNA at the DNA sequence bound at the site of said DNA-recognition domain of the RDE, and wherein the DNA-recognition domain of the RDE is fused to an active or inactive first nuclease domain via an amino acid linker, with said first nuclease domain further fused to a second active or inactive nuclease domain via a second amino acid linker attached to the C-terminus of the first nuclease domain; and
      b) a target nucleic acid comprising one or more RDE recognition domains and one or more endogenous or synthetic essential or non-essential DNAs programmed for deletion;
   ii) binding of the RDE to the target nucleic acid at a DNA sequence recognized by the DNA-recognition domain of the RDE;

iii) forming a dimer pair by said nuclease domains of the RDE on a DNA sequence that is not recognized by and is offset from the DNA-recognition domain of the RDE;
iv) single-stranded or double-stranded cleavage of the target nucleic acid at a site that is offset from the DNA sequence bound by said DNA-recognition domain of the RDE;
v) deletion of one or more base pairs at the site of cleavage, and repair of the DNA through endogenous repair and end joining processes; and
vi) repetition of steps ii) through v), wherein two or more relocalization events of the RDE cause additional removal of bases adjacent to the DNA-recognition domain.

2. The method of claim 1, wherein the target nucleic acid comprises a promoter or gene for an essential element of the RDE; an RFP promoter or gene; a GFP promoter or gene; or an sgRNA promoter or gene.

3. The method of claim 2, wherein the RDE comprises dCas9 linked to first FokI via a first linker and a second FokI linked to the first FokI via a second linker.

4. The method of claim 3, wherein the first linker comprises at least 5 amino acid residues.

5. The method of claim 3, wherein the second linker comprises at least 30 amino acid residues.

6. The method of claim 3, wherein the first FokI and the second FokI form a dimer pair for cleaving the target nucleic acid.

7. The method of claim 2, wherein the RDE comprises the DNA-recognition domain of a Zinc Finger protein, Transcription Activator Like Effector, or Cas9.

8. The method of claim 7, wherein the DNA-recognition domain comprises dCas9 associated with a guide RNA.

9. The method of claim 2, wherein the nuclease domain is selected from a homing endonuclease or a restriction enzyme.

10. The method of claim 9, wherein the nuclease domain is selected from NucA, TevI, I-SceI, ColE7, FokI, PvuII, NdeI, BsrBI, BsaI, and MMeI.

11. The method of claim 1, wherein the RDE comprises dCas9 linked to first FokI via a first linker and a second FokI linked to the first FokI via a second linker.

12. The method of claim 11, wherein the first linker comprises at least 5 amino acid residues.

13. The method of claim 11, wherein the second linker comprises at least 30 amino acid residues.

14. The method of claim 11, wherein the first FokI and the second FokI form a dimer pair for cleaving the target nucleic acid.

15. The method of claim 1, wherein the RDE comprises the DNA-recognition domain of a Zinc Finger protein, Transcription Activator Like Effector, or Cas9.

16. The method of claim 15, wherein the DNA-recognition domain comprises dCas9 associated with a guide RNA.

17. The method of claim 1, wherein the nuclease domain is selected from a homing endonuclease or a restriction enzyme.

18. The method of claim 17, wherein the nuclease domain is selected from NucA, TevI, I-SceI, ColE7, FokI, PvuII, NdeI, BsrBI, BsaI, and MMeI.

* * * * *